US012337063B2

(12) United States Patent
Rawas-Qalaji et al.

(10) Patent No.: US 12,337,063 B2
(45) Date of Patent: Jun. 24, 2025

(54) FORMULATION FOR ATROPINE SULFATE RAPIDLY-DISINTEGRATING SUBLINGUAL TABLETS

(71) Applicant: University of Sharjah, Sharjah (AE)

(72) Inventors: Mutasem Rawas-Qalaji, Sharjah (AE); Rawan S. Bafail, Sharjah (AE)

(73) Assignee: UNIVERSITY OF SHARJAH, Sharjah (AE)

( * ) Notice: Subject to any disclaimer, the term of this patent is extended or adjusted under 35 U.S.C. 154(b) by 0 days.

(21) Appl. No.: 16/329,299

(22) PCT Filed: Sep. 5, 2017

(86) PCT No.: PCT/US2017/050030
§ 371 (c)(1),
(2) Date: Feb. 28, 2019

(87) PCT Pub. No.: WO2018/045367
PCT Pub. Date: Mar. 8, 2018

(65) Prior Publication Data
US 2019/0247296 A1    Aug. 15, 2019

Related U.S. Application Data

(60) Provisional application No. 62/383,115, filed on Sep. 2, 2016.

(51) Int. Cl.
| | | |
|---|---|---|
| *A61K 9/00* | (2006.01) | |
| *A61K 9/20* | (2006.01) | |
| *A61K 31/4425* | (2006.01) | |
| *A61K 31/46* | (2006.01) | |
| *A61K 31/5513* | (2006.01) | |
| *A61K 31/5517* | (2006.01) | |
| *A61K 45/06* | (2006.01) | |
| *A61P 39/02* | (2006.01) | |

(52) U.S. Cl.
CPC ............ *A61K 9/006* (2013.01); *A61K 9/2009* (2013.01); *A61K 9/2013* (2013.01); *A61K 9/2054* (2013.01); *A61K 9/2095* (2013.01); *A61K 31/4425* (2013.01); *A61K 31/46* (2013.01); *A61K 31/5513* (2013.01); *A61K 31/5517* (2013.01); *A61K 45/06* (2013.01); *A61P 39/02* (2018.01)

(58) Field of Classification Search
None
See application file for complete search history.

(56) References Cited

U.S. PATENT DOCUMENTS

| | | | |
|---|---|---|---|
| 4,352,810 A | 10/1982 | Benschop et al. | |
| 2006/0045865 A1* | 3/2006 | Jacob | A61K 9/204 424/78.27 |
| 2012/0282335 A1* | 11/2012 | Venkatesh | A61K 31/5513 424/465 |
| 2013/0289021 A1 | 10/2013 | Volvovitz | |
| 2014/0171515 A1* | 6/2014 | Lederman | A61K 31/135 514/654 |
| 2014/0248223 A1 | 9/2014 | Myers et al. | |

FOREIGN PATENT DOCUMENTS

WO    2016054504 A1    4/2016

OTHER PUBLICATIONS

Definition for "Alkalinizing Agent" accessed from the Wikipedia website https://en.wikipedia.org on Aug. 29, 2016.
Aungst, Bruce J., Absorption Enhancers: Applications and Advances; The AAPS Journal 14(1):10-18 Mar. 2012, copyright 2011.
"CEOLUS®" microcrystalline cellulose—basic information—accessed from the Asahi Kasei's website—ceolus.com for pharmaceutical excipients; on Aug. 25, 2016.
"Microcrystalline Cellulose" (inactive ingredient) accessed from the website Drugs.com on Aug. 30, 2016.
International Search Report and Written Opinion for PCT/US17/50030 dated Nov. 13, 2017.
IPRP International Preliminary Search Report and Written Opinion for PCT/US17/50030 dated Mar. 14, 2019.

* cited by examiner

*Primary Examiner* — Patricia Duffy
*Assistant Examiner* — Garen Gotfredson
(74) *Attorney, Agent, or Firm* — MH2 Technology Law Group, LLP

(57) ABSTRACT

The invention provides atropine sulfate (AS) rapidly-disintegrating sublingual tablets (RDSTs) of improved formulation in a sublingual dosage form and methods for therapeutic use of the AS RDSTs for treatment of organophosphate (OP) exposure and acute toxicity. The AS RDSTs provide an alternative easy-to-use dosage form for the management of organophosphate toxicity. Additionally, the invention provides methods for improved formulation and quality evaluation of the atropine sulfate rapidly-disintegrating sublingual tablets.

5 Claims, 7 Drawing Sheets

FORMULATION FOR ATROPINE SULFATE RAPIDLY-DISINTEGRATING SUBLINGUAL TABLETS

FIELD OF THE INVENTION

The invention generally relates to the manufacture, evaluation, and improvement of pharmaceutical compositions, particularly to the manufacture, evaluation, and improvement of orally-disintegrating tablets for buccal and/or sublingual administration, and most particularly to an atropine sulfate (AS) rapidly-disintegrating sublingual tablet (RDST) having an improved formulation in a sublingual dosage for treatment of organophosphate (OP) exposure and acute toxicity.

BACKGROUND

An organophosphate (abbreviated as "OP" or "OPs" for organophosphates) or phosphate ester is the general term for esters of phosphoric acid. The general chemical structure is as follows:

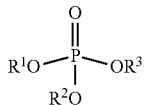

(entry for "Organophosphate" accessed from the Wikipedia website on Sep. 5, 2014). Organophosphates constitute a large group of chemical compounds as there are many different substitutes of phosphoric acid esters (Newmark J. *Neurology* 62:1590-1596, 2004).

Organophosphates are highly toxic and thus form the basis of many pesticides, insecticides, herbicides, and nerve agents (entry for "Organophosphate" accessed from the Wikipedia website on Sep. 5, 2014). Organophosphate poisoning results from exposure to organophosphates, which cause inhibition of the enzyme acetylcholinesterase (also called acetylcholine esterase) (entry for "Organophosphate Poisoning" accessed from the Wikipedia website on Sep. 5, 2014). Organophosphates phosphorylate the serine hydroxyl residue of acetylcholine esterase to form a covalent bond with acetylcholine esterase, thus inhibiting it irreversibly (entry for "Organophosphate Poisoning" accessed from the Wikipedia website on Sep. 5, 2014 and Eddleston M. et al. *Crit Care* 8:R391-R7 2004). Acetylcholine esterase is critical for nerve function and its inhibition leads to accumulation of acetylcholine in the synaptic clefts between neurons. This accumulation of acetylcholine stimulates the autonomic nervous system, nicotinic receptors, and muscarinic receptors (entry for "Organophosphate Poisoning" accessed from the Wikipedia website on Sep. 5, 2014 and Buckley N. et al. *J Toxicol Clin Toxicol* 32:61-68 1994). Overstimulation of muscarinic receptors can lead to respiratory failure and death (Eddleston M. et al. *Lancet* 371:597-607 2008). It is well documented that acute organophosphate toxicity is often fatal.

There are two sources of exposure to organophosphates, pesticides and nerve agents (i.e. chemical weapons). The epidemiological data clearly shows the importance of the management of organophosphate toxicity in reducing the number of causalities. According to the World Health Organization (WHO), in the "Impact of OPs on Health" report, there are approximately 3 million cases of organophosphate toxicity every year, with about 250,000 resulting in death. Worldwide, there are about 900,000 suicide cases every year; about 60% of these people poison themselves with organophosphates. In low-income countries that lack prepared medical centers, higher mortality rates have been recorded (Bertolote J. et al. *The Impact of Pesticides on Health: Preventing Intentional and Unintentional Deaths from Pesticide Poisoning*. In Prevention, Pesticides and Health. World Health Organization (WHO) website 2004). According to the same report, the mortality due to pesticide toxicity represents 71% of the cases in Sri Lanka, 62% in China, and 30% in India. Generally, pesticides are used excessively in all agricultural countries. In the United States alone, more than 37 types of organophosphate pesticides are used (*Pesticide Usage in the United States: History, Benefits, Risks*, and Trends. NC Cooperative Extension 1996; available from the North Carolina State University website). In 2011 and 2012, almost 7,000 organophosphate toxicity cases were reported according to the Annual Report of the American Association of Poison Control Centers' National Poison Data System (NPDS) (Bronstein A. et al. Clin Toxicol 50:911-1164 2012).

Following World War I, the Geneva Protocol of 1925 for the Prohibition of the Use in War of Asphyxiating, Poisonous, or Other Gases, and of Bacteriological Methods of Warfare was signed and took effect on Feb. 8, 1928. Although this 1925 protocol prohibited the use of chemical weapons in warfare, it did not prohibit development, production, and stockpiling of chemical weapons (*Weapons of Mass Destruction: Chemical Weapons*. United Nations Office for Disarmament Affairs website). Following World War II, the production and stockpiling was outlawed by the Chemical Weapons Convention of 1993 and took effect on Apr. 29, 1997 through the establishment of the Organization for the Prohibition of Chemical Weapons (*Weapons of Mass Destruction: Chemical Weapons*. United Nations Office for Disarmament Affairs website and Croddy E. et al. *Weapons of Mass Destruction: An Encyclopedia of Worldwide Policy, Technology, and History*. Santa Barbara, CA: ABC-CLIO 2005). Despite these disarmament attempts, nerve agents were used for the first time in 1988 during the First Gulf War between Iraq and Iran, which resulted in 40,000 deaths using sarin gas (Newmark J. *Neurology* 62:1590-1596 2004). The second documented use of nerve agents was in 1995 in a Tokyo subway by a terrorist group, which resulted in 13 deaths and 50 injuries (Bentur Y. et al. *Clin Toxicol* 44:301-306 2006). In 2013, the Assad Regime used sarin gas against the people of Syria, which resulted in 1300 deaths (*Report on the Alleged Use of Chemical Weapons in the Ghouta Area of Damascus on Aug.* 21, 2013. United Nations Mission to Investigate Allegations of the Use of Chemical Weapons in the Syrian Arab Republic, United Nations website).

The conventional, basic antidote in acute organophosphate toxicity cases is atropine sulfate (AS). The chemical structure is as follows:

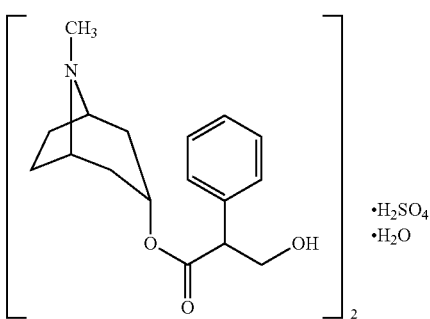

(entry from the Sigma-Aldrich company catalog, accessed online on Sep. 5, 2014). Atropine is a competitive, muscarinic acetylcholine receptor antagonist and prevents accumulated acetylcholine from activating the receptors. Acetylcholine is the main neurotransmitter used by the parasympathetic nervous system. Generally, atropine works by countering activity of glands regulated by the parasympathetic nervous system. This countering occurs because atropine is a competitive antagonist of the muscarinic acetylcholine receptor (entry for "Atropine" accessed from the Wikipedia website on Sep. 4, 2014). Atropine sulfate is capable of inhibiting the entire parasympathetic nervous system because it blocks all subtypes of muscarinic receptors. Accumulated acetylcholine is thus unable to activate the muscarinic receptors.

To date, the parenteral route is the only drug delivery route utilized for administration of atropine sulfate (AS). Atropine sulfate is administered parenterally in hospitals from a stock AS solution; or in some countries, it is given intramuscularly (IM injection) using a pre-filled auto-injector device (AtroPen®, Meridian Medical Technologies, Inc.). This pre-filled auto-injector device is designed to be used in military and community facilities (Bentur Y. et al. *Clin Toxicol* 44:301-306 2006). However, the AS pre-filled auto-injector device is not readily available for soldiers or civilians in most organophosphate toxicity cases. This conventional organophosphate toxicity management strategy, i.e. AS injection, depends on developing pre-filled auto-injectors of atropine sulfate mixed with different types of oximes (group of medications that act to re-activate acetylcholine esterase), such as pralidoxime (Eddleston M. et al. *Crit Care* 8:R391-R7 2004; Eddleston M. et al. *Lancet* 371:597-607 2008). The initial atropine sulfate (AS) dose is 2 mg, which (dose) is then doubled about every five minutes until toxicity symptoms disappear (Buckley N. et al. *J Toxicol Clin Toxicol* 32:61-68 1994) atropinization signs and symptoms are achieved.

Use of the auto-injector pens is associated with several drawbacks. First, the size (of the auto-injector pen) limits the number of pens that can be carried to allow for multiple dose administration (Rawas-Qalaji M. et al. *J Allergy Clin Immun* 117:398-403 2006). Also the high cost of the auto-injector pens limits their affordability and in turn availability to low income farmers or community facilities in low income areas at risk for organophosphate toxicity (Corcoran T. et al. *J Aerosol Med Pulm D* 26:46-55 2013). Furthermore, acute organophosphate toxicity is debilitating and the panic and stressful situation (when the OP toxicity occurs) limits the ability of the victim to get the auto-injector pen ready and inject himself/herself properly and effectively. In such conditions, risk for fracture of the syringe and/or occurrence of an administration error is high (Newmark J. *Neurology* 62:1590-1596 2004; Bentur Y. et al. *Clin Toxicol* 44:301-306 2006; Rawas-Qalaji M. et al. *J Allergy Clin Immun* 117: 398-403 2006; Hague J. et al. *Mil Med* 169:389-391 2004).

These facts and drawbacks drove the instant inventors to look into potential alternative approaches for the treatment of organophosphate toxicity, such as new formulations for drugs administrable via the oral or sublingual drug delivery route.

The sublingual route of administration is a promising alternative for atropine sulfate (AS) administration. Tablets that disintegrate or dissolve rapidly in the patient's mouth without the use of water are convenient for the elderly, young children, patients with swallowing difficulties, and in situations where water is not available. These tablets can be quickly and effectively administered, and thus (these tablets) are particularly valuable in emergency situations such as anaphylaxis and organophosphate toxicity. For these specially designed formulations, the small volume of saliva that is available is sufficient to disintegrate or dissolve a tablet in the oral cavity. The drug released from these tablets can be absorbed partially or entirely into the systemic circulation from the buccal mucosa or sublingual cavity, or can be swallowed as a solution to be absorbed from the gastrointestinal tract.

The sublingual route usually produces a faster onset of action than traditional orally-administered tablets and the portion absorbed through the sublingual blood vessels bypasses the hepatic first pass metabolic processes (Birudaraj R. et al. *J Pharm Sci* 94:70-78 2005; Motwani J. et al. *Clin Pharmacokinet* 21(2): 83-94 1991; Ishikawa T. *Chem Pharm Bull* 49: 230-232 2001; Price T. et al. *Obstet Gynecol* 89: 340-345 1997: Kroboth P. et al. *J Clin Psychopharmacol* 15(4): 259-262 1995; Cunningham F. et al. *J Clin Anesth* 6: 430-433 1994; Scavone J. et al. *Eur J Clin Pharmacol* 42: 439-443 1992: Spenard J. et al. *Biopharm Drug Dispos* 9: 457-464 1988).

Likewise, due to high buccal and sublingual vascularity, buccally- or sublingually-delivered drugs can gain direct access to the systemic circulation and are not subject to first-pass hepatic metabolism. In addition, therapeutic agents administered via the buccal or sublingual route are not exposed to the acidic environment of the gastrointestinal tract (Mitra A. et al. *Encyclopedia of Pharm Tech* 2081-2095 2002). Further, the buccal and sublingual mucosae have low enzymatic activity relative to the nasal and rectal routes. Thus, the potential for drug inactivation due to biochemical degradation is less rapid and extensive than other administration routes (de Varies et al. *Crit Rev Ther Drug Carr Syst.* 8: 271-303 1991).

The buccal and sublingual mucosae are also highly accessible, which allows for the use of tablets which are painless, easily administered, easily removed, and easily targeted. Because the oral cavity consists of a pair of buccal mucosa, tablets, such as fast disintegrating tablets, can be applied at various sites either on the same mucosa or, alternatively, on the left or right buccal mucosa (Mitra A. et al. *Encyclopedia of Pharm Tech* 2081-2095 2002). In addition, the buccal and sublingual routes could be useful for drug administration to unconscious patients, patients undergoing an anaphylactic attack, or patients suffering from the effects of acute organophosphate toxicity.

Considering the high numbers of injuries and fatalities resulting from organophosphate toxicity, there is great interest and demand in the scientific community to find a better treatment for organophosphate toxicity, particularly acute organophosphate toxicity (Dolgin E. *Nat Med* 19:1194-1195 2013 and RamaRao G. et al. *BMC* Neuroscience 15:47 2014).

Atropine sulfate (AS) is an important medication in health systems worldwide for management of organophosphate toxicity. It would be very advantageous to have non-invasive sublingual drug delivery of atropine sulfate for the treatment of acute organophosphate toxicity as a potential alternative, patient-friendly, convenient, and cost-effective dosage form.

SUMMARY OF THE INVENTION

The extensive use of organophosphates (OPs) worldwide, as pesticides and nerve agents, has resulted in millions of injuries and fatalities due to organophosphate toxicity. The current antidote for organophosphate toxicity is a 2 mg dose of atropine sulfate (AS) delivered via intramuscular (IM) injection. This dosage is administered parenterally in hospitals from a stock AS solution or is given using a pre-filled auto-injector pen. This initial 2 mg dose of AS is repeated by doubling the initial dose amount about every five minutes until toxicity symptoms disappear or a toxic level of AS is reached. To date, parenteral administration via injection is the only route utilized for atropine sulfate (AS) delivery in treatment of organophosphate toxicity.

There are many drawbacks associated with delivery of atropine sulfate (AS) via injection. First, the large size of the syringe/auto-injector pen limits the number of doses that can be conveniently carried (particularly with regard to soldiers and farmers). If the number of available doses is limited, the treatment might be insufficient and can negatively affect the efficacy of co-administered medications like oximes and benzodiazepines for complete elimination of toxicity symptoms and patient survival (Ref: Koplovitz I, Menton R, Matthews C, Shutz M, Nails C, Kelly S. Dose-response effects of atropine and HI-6 treatment of organophosphorus poisoning in guinea pigs. Drug and chemical toxicology. 1995; 18:119-36). Additionally, due to high cost, the pre-filled auto-injectors are generally unavailable in low income areas. Furthermore, acute organophosphate toxicity is debilitating and the panic and stressful situation (when the OP toxicity occurs) limits the ability of the victim to get the auto-injector pen ready and inject himself/herself properly and effectively. In such conditions, risk for fracture of the syringe and/or occurrence of an administration error is high. Therefore, based on these drawbacks, successful administration of atropine sulfate in organophosphate toxicity generally requires a heath care setting.

In response to the need for an alternative dosage form for atropine sulfate (AS), the instant inventors formulated and manufactured an exemplary formula for rapidly-disintegrating (fast-disintegrating) or dissolving sublingual tablets (RDSTs) of atropine sulfate (AS) which circumvents the aforementioned problems. They performed several quality control tests to ensure rapid and complete drug release and tested diffusion of atropine sulfate from the AS RDSTs ex vivo. These experiments confirmed, for the first time, that atropine sulfate (AS) is permeable sublingually using RDSTs formulation and has the potential to be administered using an alternative user-friendly dosage form for the treatment of emergency conditions, such as organophosphate toxicity. The formulation, manufacture, and testing of these AS RDSTs was described in the related applications: International Application No. PCT/US2015/053713 and U.S. Provisional Patent Application No. 62/058,722, the contents of each of which are hereby incorporated herein by reference.

The development of drugs for sublingual administration focuses on the fact that the sublingual route is more permeable than other routes and has an extensive network of blood vessels that aid in drug absorption (J. Swarbrick *Encyclopedia of Pharmaceutical Technology* New York, USA, CRC Press 2006). In light of this, and the success of the AS RDSTs, the instant inventors were moved to improve the formulation of the AS RDSTs.

As used herein, the phrase "improve/improving the formulation" refers to any changes or modifications made to the previously-described formulation which enhance the therapeutic effectiveness of the resulting manufactured tablets.

Improving the formulation of a drug can be achieved by altering one or more properties and/or characteristics of the drug. In this case, the instant inventors sought to optimize the sublingual permeability and absorption of atropine sulfate (AS). Two strategies reported to increase drug permeability and absorption are increasing the un-ionized portion of the drug and using penetration enhancers (T. Goswami et al. *AAPS PharmSciTech* 2016; A. M. Al-Ghananeem et al. *AAPS PharmSciTech* 7(1): E23 2006). The instant inventors designed and carried out experiments to assess the effect of modifying the pH of the absorption medium on the sublingual permeability of atropine sulfate and to assess the effectiveness of various permeability enhancers, for example sodium dodecyl sulfate (SDS), chitosan, bile salts, and palmitoyl-L carnitine chloride, on the permeability and absorption of atropine sulfate in order to optimize RDST formulation of atropine sulfate such that a new tablet, which is more user-friendly and convenient to administer than an atropine sulfate injection in emergency situations like organophosphate toxicity, can be produced. These experiments and the resulting rapidly-disintegrating tablets (RDSTs) of atropine sulfate (AS) are described herein.

In one aspect, the invention provides a pharmaceutical composition including atropine sulfate (AS).

In another aspect, the invention provides a therapeutic tablet including atropine sulfate (AS).

In another aspect, the invention provides a pharmaceutical composition including atropine sulfate (AS) and formulated for rapid disintegration in buccal or sublingual administration.

In another aspect, the invention provides a therapeutic tablet including atropine sulfate (AS) and formulated for rapid disintegration in buccal or sublingual administration.

As described herein, buccal or sublingual oral disintegrating tablets (ODTs) are distinguished from conventional sublingual tablets, lozenges, or buccal tablets by the ODTs ability to rapidly fully dissolve and/or rapidly disintegrate in less than about one minute in the mouth. These tablets are described herein as "rapidly-disintegrating sublingual tablets (RDSTs)" formulated for disintegration. These tablets can also be described as "fast-disintegrating sublingual tablets (FDSTs)." The term "about" in this context refers to times near or close to one minute and encompasses times in which the RDSTs can dissolve and still reasonably achieve the described function of rapidly fully dissolving and/or rapidly disintegrating in less than about one minute in the mouth.

In another aspect, the invention provides a pharmaceutical composition including atropine sulfate (AS) and at least one pharmaceutically-acceptable excipient and formulated for rapid disintegration in buccal or sublingual administration. The pharmaceutical composition can be, but is not limited to, a therapeutic tablet.

The phrase "pharmaceutically-acceptable excipient" refers to an inactive and non-toxic substance used in association with an active substance, i.e. in this invention atropine sulfate (AS), especially for aiding in the application/delivery of the active substance. "Inactive", in this context, refers to inactivity with regard to the activity of the active substance. Non-limiting examples of pharmaceutically-acceptable excipients are diluents, fillers, binders, disintegrants, superdisintegrants, flavorings (e.g. citric acid), sweeteners (e.g. aspartame and acesulfame potassium), lubricants, alkalizers/alkalinizing agents, and absorption enhancers/penetration enhancers/permeation enhancers. Pharmaceutically-acceptable excipients can have more than one function, a non-limiting e.g. a filler can also be a disintegrant. Additionally, pharmaceutically-acceptable excipients may also be referred to as non-medicinal ingredients (NMIs) or pharmaceutically-acceptable carriers.

A filler adds volume and/or mass to a composition to facilitate precise dosage formulation and to "fill out" the size such that the composition is practical to produce and convenient for the consumer to use. See entry for "Excipient" section 1.5 "Fillers" accessed from the Wikipedia website on Sep. 23, 2014. A non-limiting example of a filler is microcrystalline cellulose (MCC).

Microcrystalline cellulose (MCC) is refined wood pulp; more specifically a purified, partly depolymerized cellulose having short, crystalline polymer chains. MCC exhibits excellent compressibility and thus is frequently used in the manufacture of solid dose forms of drugs. MCC is commercially available in different powder grades having various properties. See entry for "microcrystalline cellulose" accessed from the website "Drugs" on Aug. 30, 2016 and entry for "CEOLUS®" accessed from the website of Asahi Kasei Corporation on Aug. 25, 2016. Non-limiting examples of MCC are CEOLUS® grades UF-702 and PH-301.

A disintegrant is a substance or mixture of substances added to a drug formulation that facilitates the breakup or disintegration of a tablet or capsule content into smaller pieces that dissolve more rapidly than in the absence of disintegrants. A superdisintegrant increases the efficiency of disintegration by decreasing the disintegration time which in turn enhances drug dissolution rate. See Mangal, M. et al. *International Journal of Pharmacy and Pharmaceutical Science Research* 2(2):26-35 2012 for a review of disintegrants and superdisintegrants. A non-limiting example of a superdisintegrant is hydroxypropyl cellulose. The hydroxypropyl cellulose can be low substituted.

A lubricant is a substance that prevents ingredients of a drug formulation from clumping together and from sticking to the tablet punches and dies. Lubricants also ensure that tablet formation and ejection can occur with low friction between the solid and die wall. See entry for "Excipient" section 1.8 "Lubricants" accessed from the Wikipedia website on Sep. 23, 2014. A non-limiting example of a lubricant is magnesium stearate.

An alkalizer or alkalinizing agent is a substance used to alter pH, particularly to raise or increase pH. See entry for "Alkalinizing Agent" accessed from the Wikipedia website on Aug. 29, 2016. Non-limiting examples of alkalizers are sodium bicarbonate, calcium carbonate, sodium citrate, potassium citrate, sodium lactate, and calcium acetate.

An absorption enhancer/penetration enhancer is a functional excipient that acts to improve the absorption of a pharmacologically-active drug, usually by enhancing membrane permeation, rather than by increasing solubility. Thus, an absorption enhancer can more specifically be referred to as a "permeation enhancer." See Aungst, Bruce J. *The AAPS Journal* 14(1):10-18 2012 for a review of absorption/permeation enhancers. Non-limiting examples of permeation enhancers are sodium dodecyl sulfate (SDS), chitosan, bile salts, palmitoyl-L carnitine chloride, and sodium glycholate (Na Gly).

The invention also encompasses a pharmaceutical composition having a formulation including from about 1 to about 20 wt % of atropine sulfate, from about 20 to about 95 wt % of microcrystalline cellulose, from about 1 to about 15 wt % hydroxypropyl cellulose, from about 0.5 to about 3 wt % magnesium stearate, from about 0.5 to about 5 wt % of sodium bicarbonate, and from about 0.5 to about 3 wt % of sodium dodecyl sulfate (SDS). The hydroxypropyl cellulose can be low substituted. The invention contemplates that any suitable range of atropine sulfate can be used. Thus, the wt % of atropine sulfate is not limited to the exemplified range of about 1 to about 20 wt % of atropine sulfate.

The invention also encompasses a pharmaceutical composition having a formulation including about 16 wt % of atropine sulfate, about 72 wt % of microcrystalline cellulose, about 8 wt % hydroxypropyl cellulose, about 1 wt % of magnesium stearate, about 2 wt % of sodium bicarbonate, and a penetration enhancer added in a specific weight depending on maximum safety weight. The penetration enhancer can one or more of: about 1 wt % of sodium dodecyl sulfate (SDS), about 0.5 wt % SDS, about 16 wt % palmitoyl carnitine chloride (PCC), about 15 wt % sodium glycholate (Na Gly), and about 20 wt % Na Gly. The hydroxypropyl cellulose can be low substituted.

In the two immediately-preceding embodiments, the term "about" refers to near or close to the disclosed quantities and encompasses quantities in which the composition can be formulated with and still reasonably achieve the described function of rapidly fully dissolving and/or rapidly disintegrating in less than about one minute in the mouth.

The invention also provides a method for manufacturing atropine sulfate (AS) tablets formulated for rapid disintegration in buccal or sublingual administration. The manufacturing method includes weighing atropine sulfate and pharmaceutically-acceptable excipients; sieving the atropine sulfate and pharmaceutically-acceptable excipients; combining and mixing the atropine sulfate and pharmaceutically-acceptable excipients to form a directly compressible formulation; and directly compressing the formulation to form the atropine sulfate tablets. The pharmaceutically-acceptable excipients can include, but are not limited to, diluents, fillers, binders, disintegrants, superdisintegrants, flavorings (e.g. citric acid), sweeteners (e.g. aspartame and acesulfame potassium), lubricants, alkalizers/alkalinizing agents, and absorption enhancers/penetration enhancers/permeation enhancers. The formulation can be directly compressed using concave punches and dies.

The manufacturing method for atropine sulfate (AS) tablets formulated for rapid disintegration in buccal or sublingual administration encompasses an embodiment in which the tiller is microcrystalline cellulose, the superdisintegrant is hydroxypropyl cellulose (can be low substituted), the lubricant is magnesium stearate, the alkalizer is sodium bicarbonate, and the permeation enhancer is sodium dodecyl sulfate (SDS). In this embodiment the combining and mixing the atropine sulfate and pharmaceutically-acceptable excipients to form a directly compressible formulation includes the steps of: a) combining the atropine sulfate with the microcrystalline cellulose and mixing to form a mixture; b) adding two thirds of the hydroxypropyl cellulose, the sodium bicarbonate, and the penetration enhancer to the mixture formed in step a) and mixing for about four minutes to form a mixture; c) mixing the magnesium stearate and the remaining one third of the hydroxypropyl cellulose to form a second mixture; and d) adding the second mixture to the mixture formed in step b) and mixing for about thirty seconds. The formulation can be directly compressed using concave punches and dies. This method achieves both internal and external positioning of the superdisintegrant.

In another aspect, the invention provides a method for treating symptoms of exposure to organophosphates (OPs) in a subject in need thereof. Prolonged exposure or exposure to excessive amounts of OPs can result in severe, acute organophosphate toxicity. The term "subject" includes any human being or animal exhibiting symptoms of exposure to organophosphates (OPs) and thus in need of treatment of the symptoms. The term "patient" is also used herein to refer to the subject. A subject could be exposed to organophosphates through pesticides or nerve agents. In addition to accidental exposure, exposure can be intended. Numerous suicides by organophosphate toxicity have been documented.

Organophosphates inhibit acetylcholine esterase, such that acetylcholine accumulates at nerve synapses and neuromuscular junctions. This accumulation of acetylcholine stimulates/activates muscarinic receptors and nicotinic receptors to stimulate the central nervous system (CNS). Thus, a patient (subject) exposed to organophosphates can exhibit any symptom resulting from excessive acetylcholine activity. The presentation of organophosphate exposure/poisoning depends upon whether the exposure/poisoning is mild, moderate, or severe. Symptoms accompanying mild exposure/poisoning include small or pinpoint pupils, painful, blurred vision, runny eyes, runny nose, excessive saliva, glassy eyes, headache, nausea, mild muscle weakness, localized muscle twitching, and/or mild agitation. Symptoms accompanying moderate exposure/poisoning include pinpoint pupils, conjunctival injection, dizziness, disorientation, coughing, wheezing, sneezing, drooling, excess phlegm, bronchorrhoea, bronchospasm, breathing difficulty, marked muscle twitching, tremors, fatigue, muscle weakness, vomiting, diarrhea, and/or urination. Symptoms accompanying severe exposure/poisoning include pinpoint pupils, confusion, agitation, convulsions, copious excessive secretions, cardiac arrhythmias, respiratory depression, respiratory arrest, and/or coma. Severe exposure/poisoning often proves fatal. See article "Organophosphate Poisoning" accessed from the Patient website on Sep. 24, 2014.

The treatment method encompasses providing a composition including atropine sulfate and at least one pharmaceutically-acceptable excipient and administering the composition to the subject. The provided composition is formulated for rapid disintegration in buccal or sublingual administration. In this method, the pharmaceutically-acceptable excipients include diluents, fillers, binders, disintegrants, superdisintegrants, flavorings (e.g. citric acid), sweeteners (e.g. aspartame and acesulfame potassium), lubricants, alkalizers/alkalinizing agents, and absorption enhancers/penetration enhancers/permeation enhancers.

A specific, albeit non-limiting, example includes microcrystalline cellulose as a filler, hydroxypropyl cellulose as a superdisintegrant, magnesium stearate as a lubricant, sodium bicarbonate as an alkalizer, and one or more of sodium dodecyl sulfate (SDS), palmitoyl carnitine chloride (PCC), and sodium glycholate (Na Gly) as a permeation enhancer. The hydroxypropyl cellulose can be low substituted.

The method can further encompass administering additional compositions to treat symptoms of organophosphate exposure/toxicity/poisoning concomitantly with the atropine sulfate rapidly-disintegrating sublingual tablets (AS RDSTs). A non-limiting example of such compositions is a cholinesterase re-activator such as an oxime or any other cholinesterase re-activator, benzodiazepine, and/or scopolamine. A specific, albeit non-limiting, example of a cholinesterase re-activator is pralidoxime chloride. A specific, albeit non-limiting, example of a benzodiazepine is midazolam, diazepam or lorazepam.

The phrase "effective amount" refers to the amount of a composition necessary to achieve the composition's intended function.

The phase "therapeutically-effective amount" refers to the amount of a composition required to achieve the desired function, i.e. treatment of the symptoms of exposure to organophosphates.

The invention also encompasses atropine sulfate (AS) rapidly-disintegrating sublingual tablets (RDSTs) produced by any of the fabrication methods and/or manufacture steps described herein.

Other objectives and advantages of this invention will become apparent from the following description taken in conjunction with the accompanying drawings, wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

A more complete understanding of the present invention may be obtained by references to the accompanying drawings when considered in conjunction with the subsequent detailed description. The embodiments illustrated in the drawings are intended only to exemplify the invention and should not be construed as limiting the invention to the illustrated embodiments.

FIG. 2 shows the cumulative atropine sulfate (AS) diffused per area ($\mu g/cm^2$) versus time from the rapidly-disintegrating sublingual tablets (RDSTs) at different pH.

FIG. 3 shows the atropine sulfate (AS) diffused percent (%) versus time from the rapidly-disintegrating sublingual tablets (RDSTs) at different pH.

FIG. 4 shows the influx of atropine sulfate (AS) versus time from the rapidly-disintegrating sublingual tablets (RDSTs) at different pH.

FIG. 5 shows the permeability of atropine sulfate (AS) versus time from the rapidly-disintegrating sublingual tablets (RDSTs) at different pH.

FIG. 6 shows the cumulative atropine sulfate (AS) diffused per area ($\mu g/cm^2$) versus time from the rapidly-disintegrating sublingual tablets (RDSTs) formulations.

FIG. 7 shows the atropine sulfate (AS) diffused percent (%) versus time from various rapidly-disintegrating sublingual tablets (RDSTs) formulations.

FIG. 8 shows the influx of atropine sulfate (AS) from various rapidly-disintegrating sublingual tablets (RDSTs) formulations.

FIG. 9 shows the permeability of atropine sulfate (AS) from various rapidly-disintegrating sublingual tablets (RDSTs) formulations.

FIG. 10 shows the cumulative atropine sulfate (AS) diffused per area (µg/cm$^2$) versus time from the rapidly-disintegrating sublingual tablets (RDSTs) formulations.

FIG. 11 shows the atropine sulfate (AS) diffused percent (%) versus time from various rapidly-disintegrating sublingual tablets (RDSTs) formulations.

FIG. 12 shows the influx of atropine sulfate (AS) from various rapidly-disintegrating sublingual tablets (RDSTs) formulations.

FIG. 13 shows the permeability of atropine sulfate (AS) from various rapidly-disintegrating sublingual tablets (RDSTs) formulations.

DEFINITIONS OF FORMULATION GROUPS (FIGS. 6-13)

Figure 1:
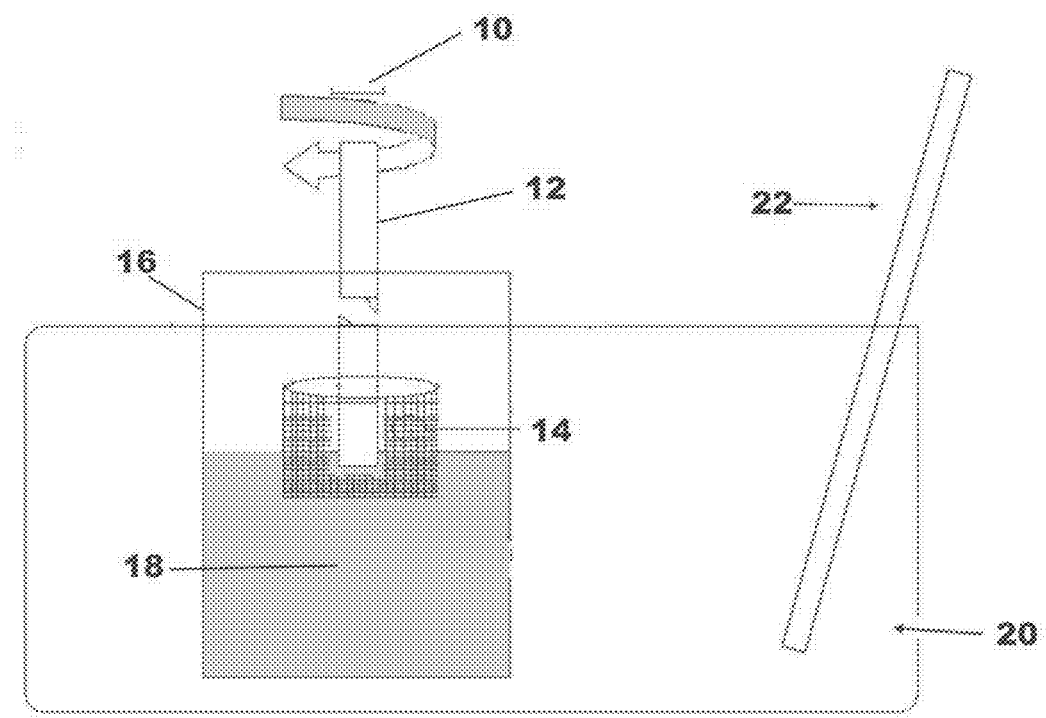
FIG. 1 is a schematic illustration of the disintegration apparatus used for carrying out the disintegration test on the rapidly-disintegrating sublingual tablets (RDSTs).
Figure 2:
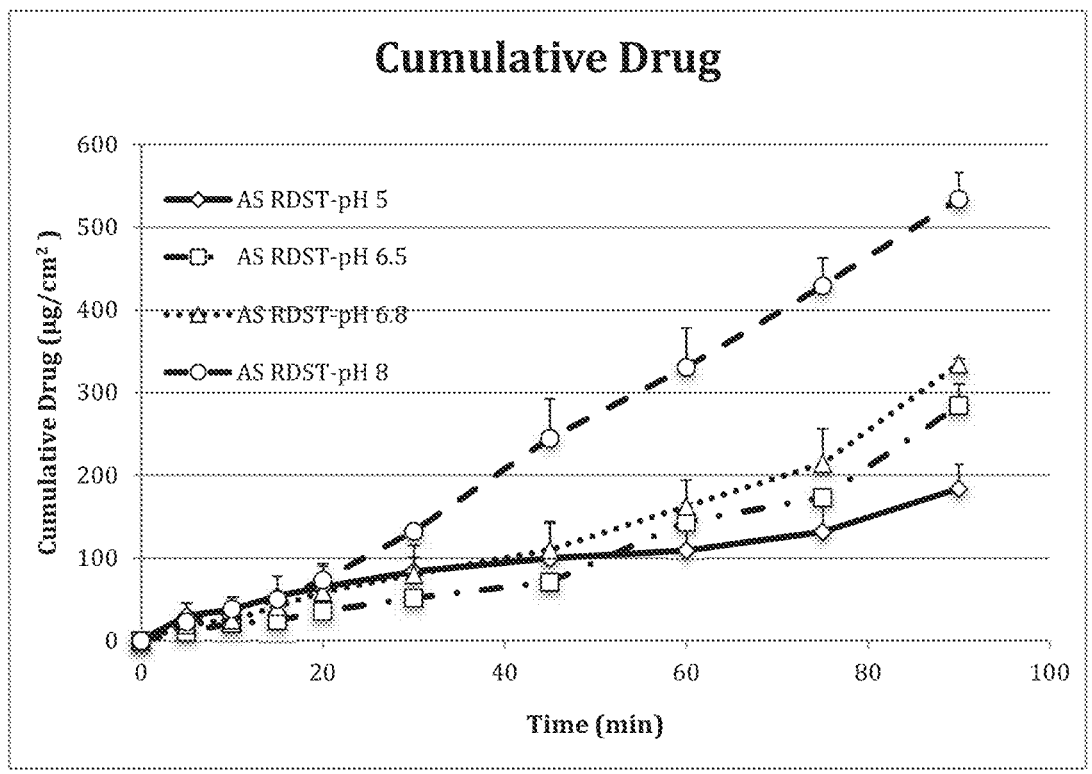
FIGS. 2-13 are graphs plotting results from the ex vivo permeation studies on the rapidly-disintegrating sublingual tablets (RDSTs).
Figure 3:
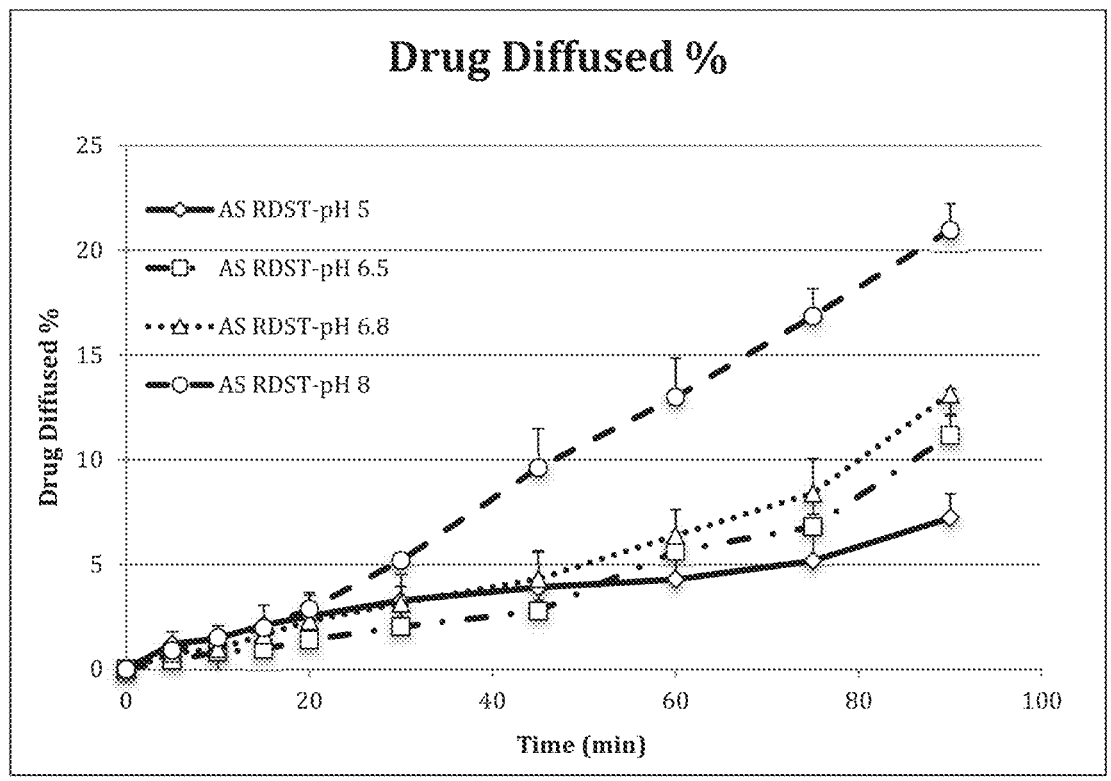
Figure 4:
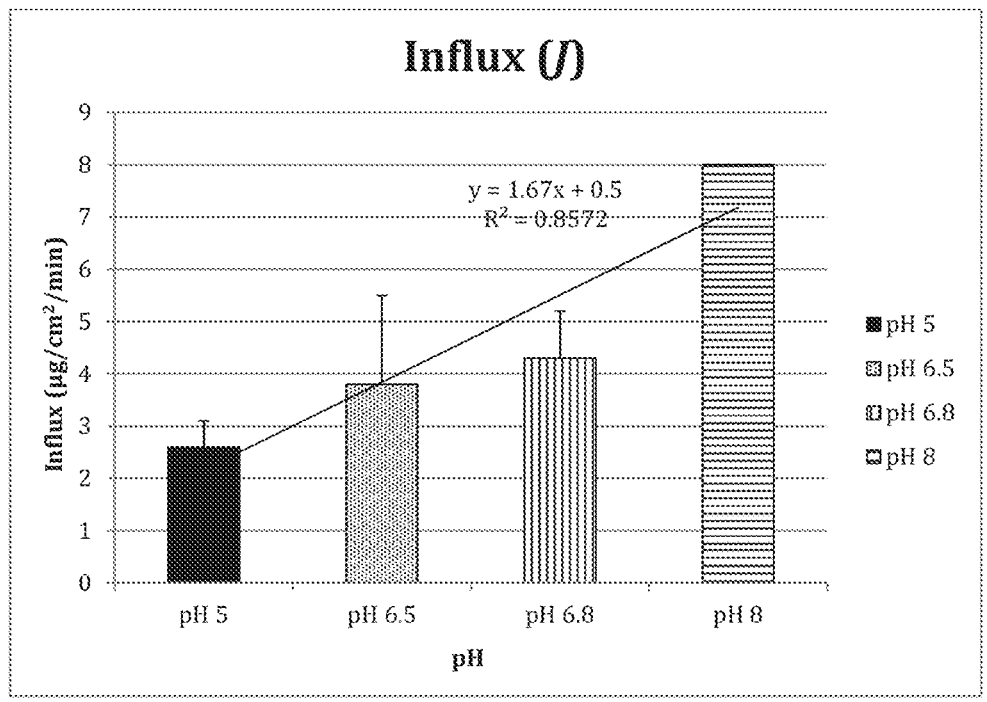
Figure 5:
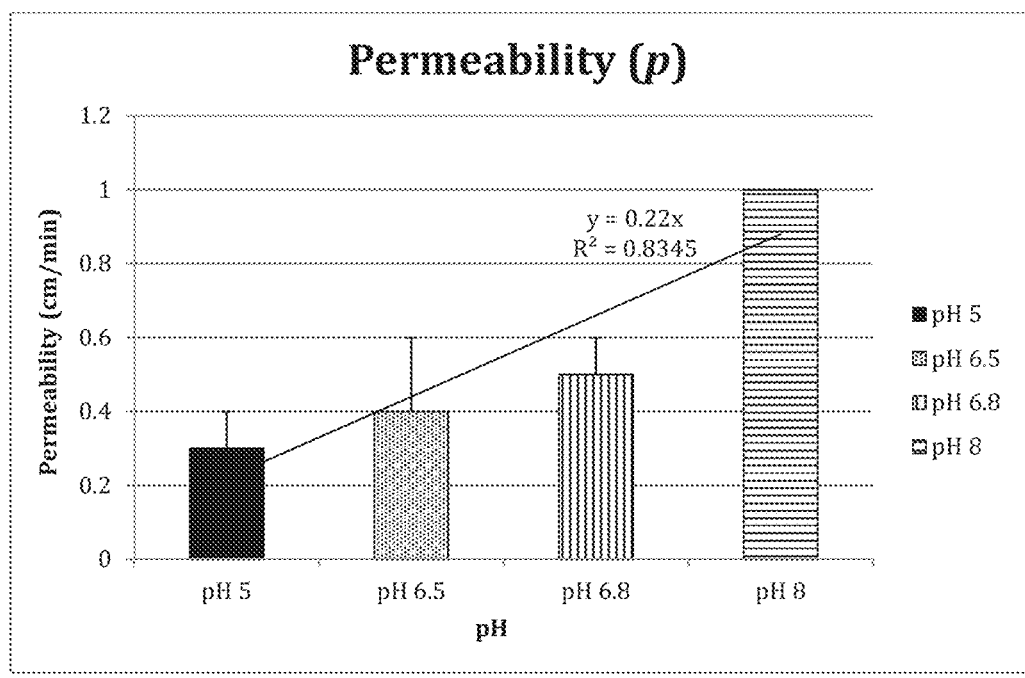
Figure 6:
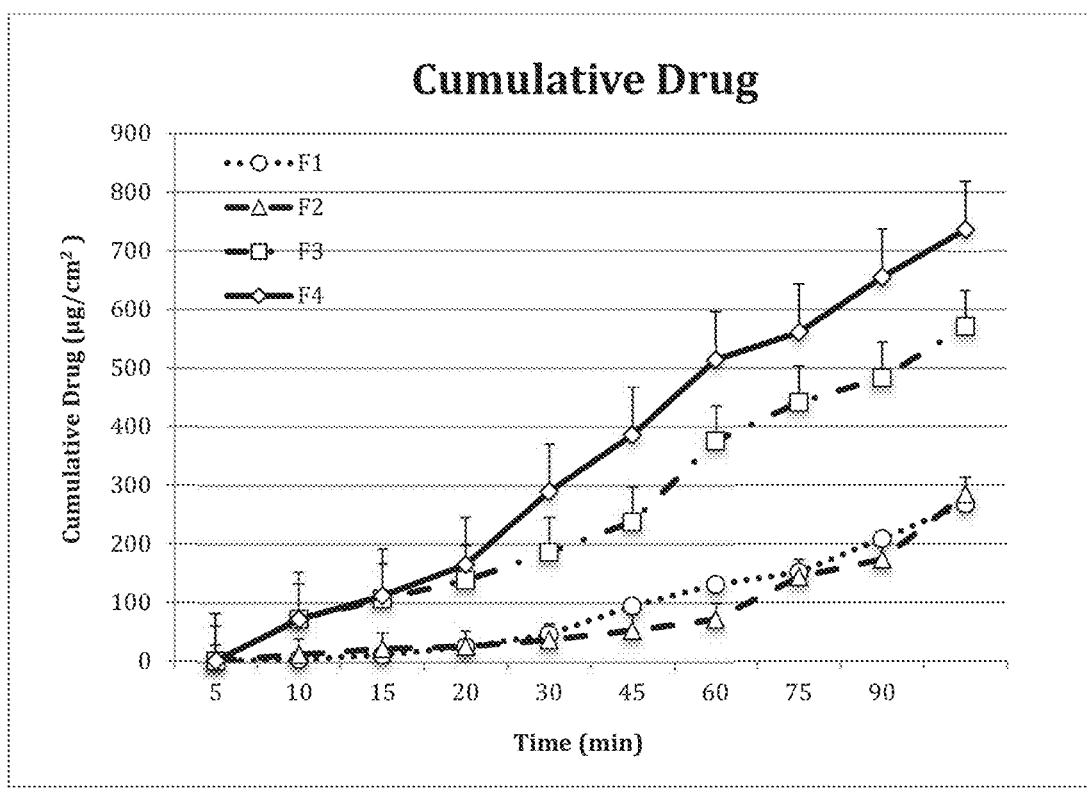
Figure 7:
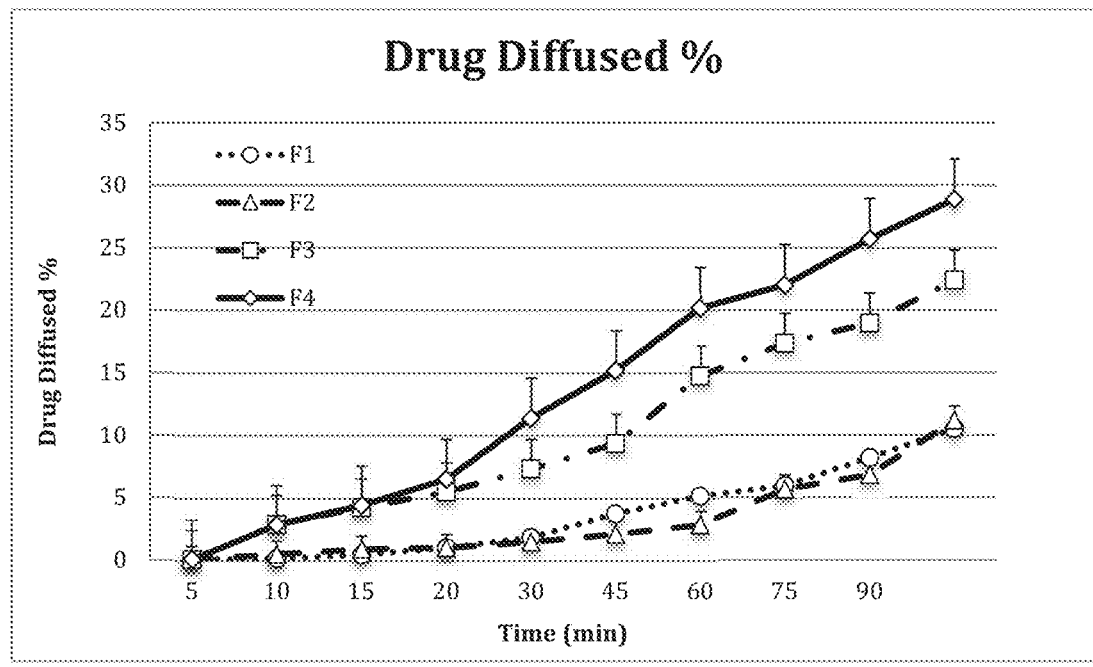
Figure 8:
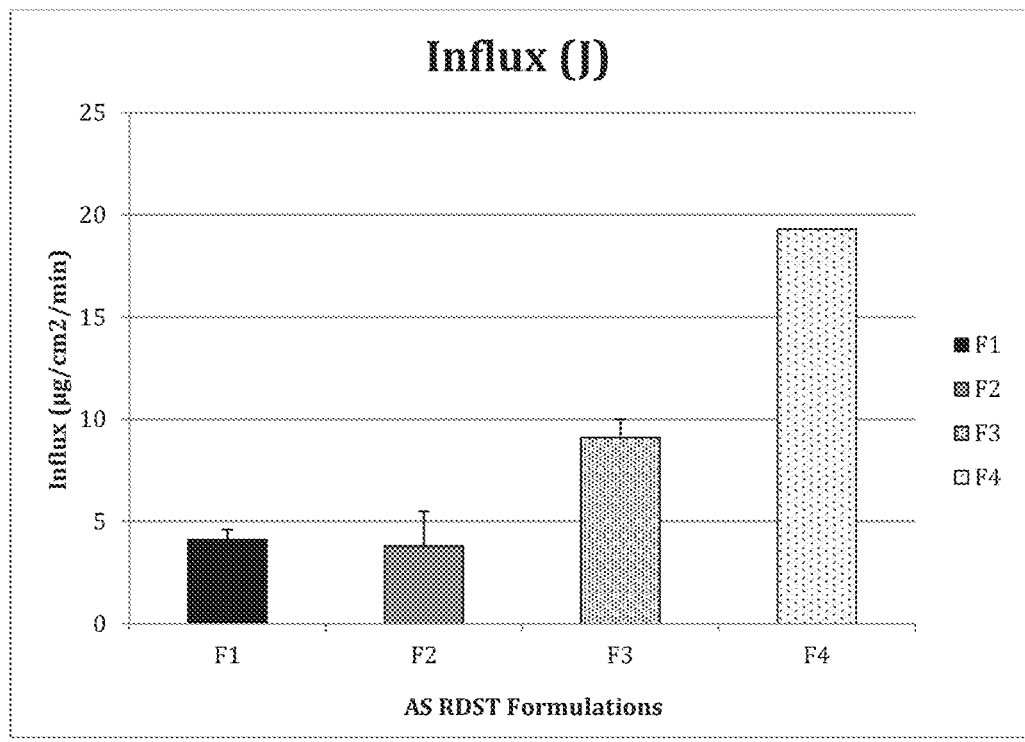
Figure 9:
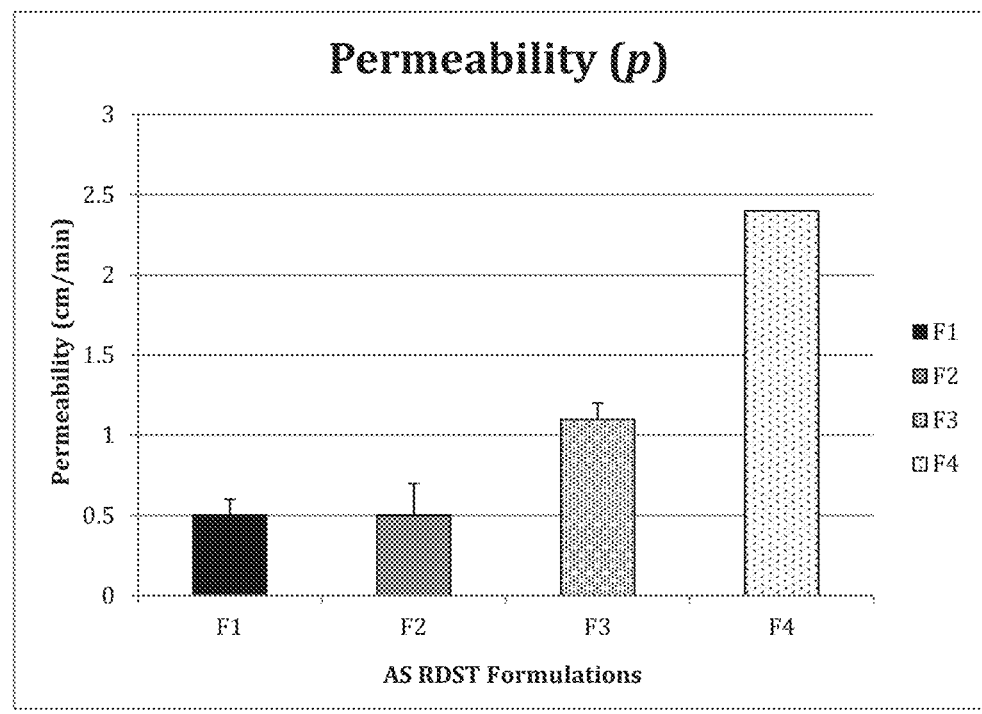

F1: 8 mg AS RDST using MCC PH-301; F2: 8 mg AS RDST using MCC UF-702; F3: 8 mg AS RDST with an alkalizer; F4-F8: 8 mg AS RDST with an alkalizer and a penetration enhancer (SDS 0.5%, SDS 1%, PCC 16%, Na Gly 15%, and Na Gly 20%, respectively); and F9-F10: 8 mg AS RDST with a penetration enhancer (SDS 1% and Na Gly 20%, respectively).

DETAILED DESCRIPTION OF THE INVENTION

For the purpose of promoting an understanding of the principles of the invention, reference will now be made to embodiments illustrated herein and specific language will be used to describe the same. It will nevertheless be understood that no limitation of the scope of the invention is thereby intended. Any alterations and further modification in the described compositions, tablets, formulations, and methods and any further application of the principles of the invention as described herein, are contemplated as would normally occur to one skilled in the art to which the invention relates.

The worldwide use of organophosphates (OPs), as pesticides and nerve agents, has been reported as causing 3 million toxicity cases per year. According to the American Association of Poison Control Centers, almost 7000 toxicity cases were reported in the last two years in the United States alone due to organophosphate use as pesticides. The recommended antidote for organophosphate toxicity is a 2 mg injection of atropine sulfate (AS). Due to the side effects and administration limitations of injections mainly outside of healthcare settings, an alternative easy-to-use dosage form of atropine sulfate would be most beneficial.

In response to the need for an alternative dosage form for atropine sulfate, the instant inventors formulated and manufactured an exemplary formula for rapidly-disintegrating or dissolving sublingual tablets (RDSTs) of atropine sulfate (AS). They performed several quality control tests to ensure rapid and complete drug release and tested diffusion of atropine sulfate from the AS RDSTs in vitro. These experiments confirmed, for the first time, that atropine sulfate (AS) is permeable sublingually using RDSTs formulation and has the potential to be administered using an alternative user-friendly dosage form for the treatment of emergency conditions, such as organophosphate toxicity. The formulation, manufacture, and testing of these AS RDSTs was described in the related applications: International Application No. PCT/US2015/053713 and U.S. Provisional Patent Application No. 62/058,722.

The development of drugs for sublingual administration focuses on the fact that the sublingual route is more permeable than other routes and has an extensive network of blood vessels that aid in drug absorption (J. Swarbrick *Encyclopedia of Pharmaceutical Technology* New York, USA, CRC Press 2006). In light of this, and the success of the AS RDSTs, the instant inventors were moved to improve the formulation of the AS RDSTs to optimize the sublingual permeability and absorption of atropine sulfate (AS).

Two strategies reported to increase drug permeability and absorption are increasing the un-ionized portion of the drug and using penetration enhancers (T. Goswami et al. *AAPS PharmSciTech* 2016; A. M. Al-Ghananeem et al. *AAPS PharmSciTech* 7(1): E23 2006). The instant inventors designed and carried out experiments to assess the effect of modifying the pH of the absorption medium on the sublingual permeability of atropine sulfate and to assess the effectiveness of various permeability enhancers, for example sodium dodecyl sulfate (SDS), chitosan, bile salts, and palmitoyl-L carnitine chloride, on the permeability and absorption of atropine sulfate in order to optimize RDST formulation of atropine sulfate such that a new tablet, which is more user-friendly and convenient to administer than an atropine sulfate injection in emergency situations like organophosphate toxicity, can be produced.

These experiments and results are described herein below.
Methods:

The Effect of Filler Grade on the Physical Properties of Atropine Sulfate Rapidly-Disintegrating Sublingual Tablets A previously-developed RDST containing AS 8 mg using MCC grade PH-301 (F1) as filler (Table 1A), resulted in rapid tablet disintegration, however, on the expense of tablet hardness (International Application No. PCT/US15/53713). Therefore, a newer MCC grade UF-702 (F2) (Table 1A) was investigated to optimize the physical properties of AS RDSTs. All manufactured tablets were tested for quality control as described herein.

Evaluation of the Effect of Alkalinizing Excipients on Modifying the pH of the Absorption Medium An excipient influences the permeation of a drug by modifying the pH of the drug's microenvironment. They affect the permeation, absorption, and bioavailability of the drug by altering drug ionization. An un-ionized drug has higher permeability than an ionized drug.

For the purpose of alkalizing the pH of the medium, excipients at various concentrations were evaluated to increase atropine sulfate (AS) permeability and absorption by increasing its un-ionized concentration.

Different concentrations, 0.5% or 1%, of sodium bicarbonate (Na Bicarb), calcium carbonate (Ca Carb), or sodium citrate (Na Cit) were dissolved in 2 mL water (n=5) and their pH was measured. The pH readings from various samples were statistically compared at significance level of p<0.05. The excipient that was able to modify the pH of the diffusion medium the most, sodium bicarbonate, was incorporated in the AS RDST formulation (F2) to assess the effect of modifying the medium's pH on the sublingual permeation of AS.

Evaluation of the Effect of pH and the Degree of Ionization on the Sublingual Permeation of Atropine Sulfate RDSTs containing AS 8 mg and weighing 50 mg (F2) were developed and manufactured by direct compression as described herein (Table 1A). All manufactured tablets were tested for quality control as described herein.

Atropine sulfate (AS) permeability was evaluated through an excised porcine sublingual membrane using static vertical Franz diffusion cells as described herein. A phosphate acetate buffer was used to prepare a wide range of buffers, buffers at pH 5, 6.5, 6.8, or 8, to be used in the donor chamber to facilitate tablet disintegration and dissolution at the specific pH.

Evaluation of the Effect of Filler Grade, Alkalizing Excipients, and Penetration Enhancers on the Sublingual Permeation of Atropine Sulfate Some excipients have the ability to enhance drug absorption through the buccal and intestinal membranes by transient widening of the tight junctions of the cells in the membranes. However, the choice of excipient used depends on the physicochemical properties of the target site of absorption. Various penetration enhancers can be tested and used to enhance AS sublingual permeation by passive diffusion. A permeation enhancer (F4: SDS 0.5%, F5: SDS 1%, F6: PCC 16%, F7: Na Gly 15%, F8: Na Gly 20%) plus an alkalizer 1% sodium bicarbonate, were incorporated into AS RDST formulation (F4-F8 formulations), as examples for a commonly used penetration enhancer and an alkalizer, to evaluate and demonstrate its effect on enhancing the sublingual permeation of AS.

The ex vivo sublingual permeation of AS was evaluated from ten AS RDST formulations, 8 mg AS RDST using MCC PH-301 as a filler (F1), 8 mg AS RDST using MCC UF-702 as a filler (F2), 8 mg AS RDST using MCC UF-702 with an alkalizer (F3), and 8 mg AS RDST using MCC UF-702 with an alkalizer and a penetration enhancer (F4-F8) (Table 1A, F1-F5 and Table 1B, F6-F10). AD RDST formulations containing 8 mg AS and only a penetration enhancer, SDS 1% (F9) or Na Gly 20% (F10), were also tested to evaluate the permeability-enhancing effect without an alkalizer (Table 1B).

AS permeability was evaluated through an excised porcine sublingual membrane using static vertical Franz diffusion cells as described herein. Phosphate buffer (pH 6.5) was used for F and F2 and deionized water was used for F3 and F4 in the donor chamber to facilitate tablet disintegration and dissolution. All manufactured tablets were tested for quality control as described herein.

Formulation:
Powder Composition

Ten AS RDST exemplary formulations were manufactured as described below. The compositions of AS RDSTs are listed below. Table 1A and Table 1B.

TABLE 1A

Atropine Sulfate (AS) Rapidly Disintegrating Sublingual Tablets (RDSTs) Formulations

| No. | Ingredient | Function | F1 | F2 | F3 | F4 | F5 |
|---|---|---|---|---|---|---|---|
| 1 | Atropine Sulfate, mg (%) | API | 8.00 (16%) | 8.00 (16%) | 8.00 (16%) | 8.00 (16%) | 8.00 (16%) |
| 2 | Microcrystalline Cellulose (Ceolus ® PH-301), mg (%) | Filler | 37.35 (74.7%) | — | — | — | — |
| 3 | Microcrystalline Cellulose (Ceolus ® UF-702), mg (%) | Filler | — | 37.35 (74.7%) | 36.45 (72.9%) | 36.2 (72.4%) | 36 (72.0%) |
| 4 | Low-Substituted Hydroxypropyl Cellulose (LH-11 ®), mg (%) | Superdisintegrant | 4.15 (8.3%) | 4.15 (8.3%) | 4.05 (8.1%) | 4.0 (8%) | 4.0 (8%) |
| 5 | Magnesium Stearate, mg (%) | Lubricant | 0.5 (1%) | 0.5 (1%) | 0.5 (1%) | 0.5 (1%) | 0.5 (1%) |
| 6 | Sodium Bicarbonate, mg (%) | Alkalizer | — | — | 0.5 (1%) | 0.5 (1%) | 0.5 (1%) |
| 7 | Penetration Enhancer, mg (%) | Permeation Enhancer | — | — | — | 0.25 (0.5%) | 0.5 (1%) |
| | Total Tablet Weight, mg (%) | | 50.00 (100%) | 50.00 (100%) | 50.00 (100%) | 50.00 (100%) | 50.00 (100%) |

TABLE 1B

Atropine Sulfate (AS) Rapidly Disintegrating Sublingual Tablets (RDSTs) Formulations

| No. | Ingredient | Function | F6 | F7 | F8 | F9 | F10 |
|---|---|---|---|---|---|---|---|
| 1 | Atropine Sulfate, mg (%) | API | 8.00 (16%) | 8.00 (16%) | 8.00 (16%) | 8.00 (16%) | 8.00 (16%) |
| 2 | Microcrystalline Cellulose (Ceolus ® PH-301), mg (%) | Filler | — | — | — | — | — |
| 3 | Microcrystalline Cellulose (Ceolus ® UF-702), mg (%) | Filler | 29.25 (58.5%) | 29.7 (59.4%) | 27.4 (54.9%) | 36.9 (73.8%) | 28.35 (56.7%) |
| 4 | Low-Substituted Hydroxypropyl Cellulose (LH-11 ®), mg (%) | Superdisintegrant | 3.25 (6.5%) | 3.3 (6.6%) | 3.05 (6.1%) | 4.1 (8.2%) | 3.15 (6.3%) |
| 5 | Magnesium Stearate, mg (%) | Lubricant | 0.5 (1%) | 0.5 (1%) | 0.5 (1%) | 0.5 (1%) | 0.5 (1%) |
| 6 | Sodium Bicarbonate, mg (%) | Alkalizer | 0.5 (1%) | 0.5 (1%) | 0.5 (1%) | — | — |
| 7 | Penetration Enhancer, mg (%) | Permeation Enhancer | 8.0 (16%) | 7.5 (15%) | 10.0 (20%) | 0.5 (1%) | 10.0 (20%) |
| | Total Tablet Weight, mg (%) | | 50.00 (100%) | 50.00 (100%) | 50.00 (100%) | 50.00 (100%) | 50.00 (100%) |

Tables 1A and 1B: Atropine Sulfate (AS) Rapidly Disintegrating Sublingual Tablets (RDSTs) Formulations:
F1: 8 mg AS RDST using MCC PH-301; F2: 8 mg AS RDST using MCC UF-702; F3: 8 mg AS RDST with an alkalizer; F4-F8: 8 mg AS RDST with an alkalizer and a penetration enhancer (SDS 0.5%. SDS 1%. PCC 16%. Na Gly 15%, Na Gly 20%, respectively): and F9-: 10: 8 mg AS RDST with a penetration enhancer (SDS 1% and Na Gly 20%, respectively).

Powder Mixing and Sieving

All powders were sieved before mixing using sieve number 230 (63 µm). Atropine sulfate (Sigma-Aldrich Chemical Company, St. Louis, MO) was mixed with microcrystalline cellulose (Asahi Kasei Chemicals Corp, Tokyo, Japan) by manual geometric method.

The mixing procedure was then optimized to achieve both internal and external positioning of the superdisintegrant; i.e. low-substituted hydroxypropyl cellulose. In the method of internal and external positioning, the superdisintegrant is divided into two portions. One portion is added before granule formation (internal) and the remaining portion is added to the granules (external) with mixing prior to compression. When both internal and external methods are used, the extragranular superdisintegrant portion breaks the tablet into granules and the granules further disintegrate to release the active substance by the intragranular disintegrant portion (Kumar G. et al. *Journal of Global Pharma Technology* 4(02): 1-12 2012 and Rawas-Qalaji et al. *AAPS PharmSciTech* 7:E41 2006). Two-thirds of the low-substituted hydroxypropyl cellulose (Shin-Etsu Chemical Co, Tokyo, Japan) with or without sodium dodecyl sulfate (SDS) (Sigma-Aldrich Chemical Company, St. Louis, MO), as an example for penetration enhancers, and sodium bicarbonate (Sigma-Aldrich Chemical Company, St. Louis, MO), as an example for alkalizers, were mixed with the powder mixture using a three dimensional manual mixer (Inversina, Bioengineering AG, Wald, Switzerland) for 4 minutes. Magnesium stearate (Alfa Aesar, Haverhill, MA) and the remaining one-third of low-substituted hydroxypropyl cellulose were manually mixed and then added to powder mixture to be mixed for additional 30 seconds.

Tablet Manufacturing

The mixture was then compressed into tablets via direct compression. In direct compression an active agent, i.e. drug, is blended with a variety of excipients, lubricated, and compressed (Kumar G. et al. *Journal of Global Pharma Technology* 4(02): 1-12 2012). The direct compression was carried out using 3"/16" concave punches and dies and a rotary mini press-I (GlobePharma. New Brunswick, NJ).

Quality Control Tests:

The manufactured tablets were tested for content uniformity, weight variation, and friability using the United States Pharmacopeia (USP) standard tests and limits. Due to lack of an accurate USP test that can discriminate small differences between RDSTs, tablet disintegration and dissolution were tested using the inventor's developed apparatuses and procedures that can detect small differences between tablets. RDSTs wetting time and water uptake were tested as well using modified procedures.

Content Uniformity and Weight Variation Tests

According to USP, content uniformity test is performed for tablets that contain less than 25 mg or less than 25% of the active material and should be within 90-110% of the labeled amount (USB/NF. Official Monograph: Atropine Sulfate Tablet. In: *United States Pharmacopeia*. 37/32 ed. Rockville, MD: United States Pharmacopeia Convention, Inc. 2014, pages 1878-1879). Both content uniformity and weight variation tests were performed according to the USP standards for all AS RDST formulations. Tablet content was analyzed by high-performance liquid chromatography (HPLC) using the standard USP procedures for analysis of atropine sulfate (AS) injection (USB/NF. *Physical Tests: <905> Uniformity of Dosage Units*. In: United States Pharmacopeia 37/32 ed. Rockville, MD: United States Pharmacopeia Convention, Inc. 2014, pages 491-494).

Breaking Force and Friability Tests

The AS RDSTs were tested (breaking force) according to the USP guidelines (USP/NF. General Chapters: <1217> *Tablet Breaking Force*. In: United States Pharmacopeia. 37/32 ed. Rockville, MD: United States Pharmacopeia Convention, Inc. 2014, pages 1146-1148) using Hardness Tester LIH-3 (Vanguard, Spring, TX).

Further, according to the standard USP Friability Test (USP/NF. General Chapters: <1216> *Tablet Friability*. In: United States Pharmacopeia. 37/32 ed. Rockville, MD: United States Pharmacopeia Convention, Inc. 2014, pages 1145-1146), sixty five tablets that weighed 6.5 g were tested using the USP Friability Tester (Pharma Test Apparatebau, GmbH, Hainburg, Germany).

Disintegration Test

The disintegration test is one of the standard USP tests. However, the current official USP standard test does not discriminate between small formulation differences. Thus, the instant inventors developed an alternative disintegration test for RDSTs.

Apparatus for Disintegration Test

The disintegration apparatus used for carrying out the disintegration test on the rapidly-disintegrating sublingual tablets (RDSTs) is illustrated schematically in FIG. 1 and includes a motor 10 with a rotating shaft 12, a stainless steel round basket 14, a stainless steel wire screen at the base (bottom) and height (walls) of the basket, a glass beaker 16 containing warmed fluid, and a water bath 20 quipped with a thermostat 22. The rotating shaft has a speed rate of 40±10 rpm, a diameter of 8±2 mm, and a length of 220±20 mm. The stainless steel round basket has a diameter of 38.5±1 mm, a height of 23±2 mm, and a welded seam. The stainless wire screen at the bottom (base) of the basket is connected to the rotating shaft at its center and has apertures of 0.36-0.44 mm and a wire diameter of 0.22-0.31 mm. The glass beaker has a diameter of 70±10 mm, a height of 90±10 mm, and a volume of 350 ml. In use, the glass beaker contains 150±5 ml of a suitable warmed fluid; i.e. water at a temperature of 37±2 CO. The fluid level in the water bath has a height of about 100 mm. In use, the basket is partially submerged in the warmed fluid to a depth of about 10±2 mm and then the basket is rotated to facilitate table disintegration. It should be noted that the values and ranges set forth above are exemplary only as the invention contemplates other suitable values and ranges.

Example Test Procedure

1. Immerse the stainless steel basket to a depth of 10 mm into the warmed fluid.
2. Rotate the basket at a speed of 40 rpm.
3. Randomly select six tablets to test.
4. Drop one tablet (one dosage unit) at a time into the rotating basket.
5. Record the time required (in seconds) for complete disintegration of the tablet.

Six tablets are selected to test based on the similar number of tablets used in the official USP standard disintegration test. The apparatus can additionally include a built-in stop that starts and stops automatically through connection to an attached sensor. The times can also be recorded using a manual stop watch.

Disintegration does not necessarily imply complete solution of the tablet. According to the USP standards, complete disintegration is defined as that state in which any residue of the tablet, except fragments of insoluble ingredients and/or coating, remaining on the wire screen is a soft mass having no palpably firm core (U.S. Pharmacopeia, General Chapter 701 "Disintegration" accessed from the internet on Sep. 17, 2014).

Wetting Test

The tablet wetting time was measured according to a previously-modified non-USP Wetting Test (WT) designed to simulate the low fluid volume and static motion available in the oral cavity and to better discriminate between small differences in formulation in the presence of limited fluid volume (Rawas-Qalaji M. et al. *Drug Dev Ind Pharm* 33:523-530 2007; Rawas-Qalaji M. et al. *AAPS PharmSciTech* 7:E72-E8 2006).

Six tablets were randomly selected and tested. One tablet was placed on double folded tissue paper in a dish having about 6 ml of water. The time for complete wetting of the tablet is recorded as the wetting time (Shukla, D. et al. *Sci Pharm* 77:327-341 2009).

Dissolution Time

Dissolution testing is a means of identifying and proving the availability of active drug materials in their delivered form. A dissolution test simulates the availability of active substance and allows prediction of the time for complete release of the material from the dosage form (*Tablet Dissolution* in the section "Analytical Products" accessed from the website of Pharma Test on Sep. 17, 2014).

Dissolution of the AS RDSTs was measured according to a previously modified non-USP dissolution test designed to simulate the low fluid volume and static motion available in mouth cavity and to better discriminate between small formulation differences in the presences of limited fluid volume (Rachid, O. et al. *AAPS PharmSciTech* 12:544-552 2011).

Six tablets were randomly selected and tested. Drug released and dissolved from each tablet after 60 seconds was analyzed by High Performance Liquid Chromatography (HPLC) using the standard USP procedure for analyzing atropine sulfate (AS) injections (USP/NF. Official Monograph: Atropine Sulfate Injection. In: *United States Pharmacopeia*. 37/32 ed. Rockville, MD: United States Phamacopeial Convention, Inc. 2014, pages 1875-1876).

Water Uptake Test

Water uptake was measured to test the ability of the tablets to uptake and hold water to swell and dissolve atropine sulfate (AS) within the tablet. The volume of water up-taken by each tablet was measured by weighing the tablet before and after adding the water droplets. Water was added dropwise, using a glass pipette, to the top of a pre-weighted tablet placed on analytical balance (d=0.01 mg) until water starts oozing outside the tablet and tablet could not hold any more water.

The percentage of water uptake was calculated using the following equation:

Water uptake %=(weight of wet tablet−weight of dry tablet)×100/weight of dry tablet Ex Vivo Sublingual Permeation Studies of Atropine Sulfate (AS):

The ex vivo permeation of atropine sulfate rapidly-disintegrating sublingual tablets (AS RDSTs) was performed using static vertical jacketed Franz Cells with an OD of 20 mm and a reservoir volume of 20±1 mL (PermeGear Inc., Hellertown, PA). A dissected porcine sublingual membrane was used as the diffusional membrane.

A receptor chamber with a magnetic stirrer was filled with phosphate buffer, pH 7.4 (which represent the pH of the blood). Before the beginning of each experiment, air bubbles were removed after mounting the membrane between the donor and receptor chambers. The water bath was set at 37° C. and water was circulated in the jacketed Franz Cells. The mounted membranes were equilibrated with the diffusion medium from both sides for 30 min and were checked for leaks.

An AS RDST was placed at the center of the donor chamber on the membrane at $T_0$ and 2 mL of distilled water or specific buffer with a specific pH was added to facilitate tablet disintegration and dissolution. Aliquots of 200 μL were withdrawn from the receptor chamber using 6-inch needles (Popper &Sons, Inc, New Hyde Park, NY) and 1 mL syringes at 5, 10, 15, 20, 30, 45, 60, 75, and 90 min. The volumes withdrawn were replenished with fresh medium. Samples were transferred to HPLC vials for HPLC analysis using a UV detector according to the standard USP method for analyzing AS injection (USP/NF. Official Monograph: Atropine Sulfate Injection. In: *United States Pharmacopeia*. 37/32 ed. Rockville, MD: United States Phamacopeial Convention, Inc. 2014, pages 1875-1876).

Statistical Analysis

The mean±SD cumulative diffused atropine sulfate (AS) per area (μg/cm$^2$) and percentage of diffused AS for each RDST formulation were calculated. The mean±SD AS influx; J (μg/cm$^2$/min), and lag time, tL (min); were calculated from the slope and the intercept with the x-axis of each graph. Also, AS permeability; P (cm/min) was calculated by dividing J by AS concentration in the donor chamber at $T_0$. The area under the curve of diffused AS per area; $JAUC_{0-90}$ (μg/cm$^2$/min) was calculated using NCSS statistical software (NCSS, Kaysville, UT). Data were statistically compared by T-test, one-way ANOVA and Tukey-Kramer tests using NCSS statistical. Differences were considered to be statistically significant at $p<0.05$.

Results:

Quality Control Tests

Quality control tests of manufactured atropine sulfate rapidly-disintegrating sublingual tablets (AS RDSTs) are presented in Tables 2A-2B.

TABLE 2A

Quality Control Tests of Atropine Sulfate (AS) Rapidly Disintegrating Sublingual Tablets (RDSTs)*

| | TEST | | | | |
|---|---|---|---|---|---|
| | F1 | F2 | F3 | F4 | F5 |
| Thickness of Tablet (mm) | 3.1 | 3.1 | 3.1 | 3.1 | 3.2 |
| Diameter of Tablet (mm) | 4.7 | 4.7 | 4.7 | 4.7 | 4.7 |
| Content Uniformity (%) | 100 ± 1.5 | 102.8 ± 3.7 | 106 ± 2.1 | 95.3 ± 2.1 | 94.1 ± 0.4 |
| Weight Variation (%) | 98.9 ± 1.6 | 102.8 ± 3.6 | 106.3 ± 2.6 | 95.4 ± 2.3 | 94.3 ± 0.9 |
| Breaking Force (Kgf) | 1.5 ± 0.1 | 2.5 ± 0.2 | 2.4 ± 0.2 | 2.3 ± 0.2 | 2.1 ± 0.2 |
| Friability (loss %) | 0.09 | 0.02 | 0.02 | 0.02 | 0.07 |
| Disintegration Time (sec) | 13.9 ± 0.4 | 5.3 ± 0.6 | 9 ± 0 | 7 ± 1 | 3.7 ± 0.6 |
| Drug Dissolved (%)§ | 88.5 ± 14.2 | 99.4 ± 6.2 | 99.8 ± 1.4 | 106.1 ± 5.3 | 126.6 ± 7.9 |
| Wetting Time (sec) | 11 ± 1 | 17.3 ± 0.9 | 16.9 ± 1.1 | 17.3 ± 1.2 | 10.0 ± 0.6 |
| Water Uptake (%) | 229 ± 12 | 302.7 ± 16 | 281 ± 8.4 | 280.9 ± 3.6 | 2.95 ± 12 |

TABLE 2B

Quality Control Tests of Atropine Sulfate (AS) Rapidly Disintegrating Sublingual Tablets (RDSTs)*

| | TEST | | | | |
|---|---|---|---|---|---|
| | F6 | F7 | F8 | F9 | F10 |
| Thickness of Tablet (mm) | 3.1 | 3.7 | 3.7 | 3.8 | 3.8 |
| Diameter of Tablet (mm) | 4.7 | 4.7 | 4.7 | 4.7 | 4.7 |
| Content Uniformity (%) | 98.3 ± 3.4 | 95.2 ± 4.4 | 88.4 ± 0.8 | 110.2 ± 2.6 | 97.2 ± 2.2 |
| Weight Variation (%) | 99.9 ± 1.2 | 95.5 ± 2.1 | 89.5 ± 1.3 | 107.8 ± 1.4 | 97.2 ± 1.7 |
| Breaking Force (Kgf) | 2.0 ± 0.1 | 2.1 ± 0.2 | 1.9 ± 0.1 | 2.2 ± 0.2 | 2.2 ± 0.3 |
| Friability (loss %) | 0.4 | 0.03 | 0.05 | 0.09 | 0.08 |
| Disintegration Time (sec) | 12.3 ± 1.2 | 8.0 ± 0.0 | 10.3 ± 0.6 | 9.7 ± 0.6 | 7.0 ± 0.0 |
| Drug Dissolved (%)§ | 86.4 ± 10.3 | 75.3 ± 8.0 | 101.5 ± 5.0 | 92.9 ± 6.0 | 91 ± 4.7 |
| Wetting Time (sec) | 35.0 ± 0.9 | 13.3 ± 1.2 | 38.5 ± 2.3 | 37.8 ± 0.9 | 18.7 ± 0.8 |
| Water Uptake (%) | 276 ± 12 | 274 ± 6 | 263 ± 6 | 293 ± 12 | 241 ± 10 |

Tables 2A and 2B: Quality Control Tests of Atropine Sulfate (AS) Rapidly Disintegrating Sublingual Tablets (RDSTs)*
F1: 8 mg AS RDST using MCC PH-301; F2: 8 mg AS RDST using MCC UF-702; F3: 8 mg AS RDST with an alkalizer; F4-F8: 8 mg AS RDST with an alkalizer and a penetration enhancer (SDS 0.5%. SDS 1%. PCC 16%, Na Gly 15%, Na Gly 20%, respectively); and F9-F10: 8 mg AS RDST with a penetration enhancer (SDS 1% and Na Gly 20%, respectively).
*Results are presented as mean±SD.
§ Drug dissolution was measured for 60 seconds.

The Effect of the Filler Grade on the Physical Properties of Atropine Sulfate Rapidly-Disintegrating Sublingual Tablets The Mean (±SD) angle of repose of the powder mixture for formulation F2 (32°±0.5°) was significantly lower (p<0.05) than formulation F1 (42°±2°). Breaking force of F1 (1.5±0.1 kgf) was significantly lower (p<0.05) than F2 (2.5±0.2 kgf). Formulation F2 had significantly (p<0.05) faster disintegration time (5.3±0.6 sec) and higher water uptake (302.7±16%) compared to formulations F1 (13.9±0.4 sec and 229±12%). Wetting time of both F1 and F2 formulations were fast and drug dissolution was high (Table 2A).

Thus, the selection of MCC grade UF-702 as a filler significantly impacted RDSTs characteristics and enhanced both tablet breaking force and disintegration time at the same time to enhance the drug physical properties.

The Effect of Alkalinizing Excipients on Modifying the pH of the Absorption Medium The pH of 1% sodium bicarbonate (Na Bicarb) (8.1±0.3) was significantly higher (p<0.05) than pH of 0.5% Na Bicarb (7.2±0.2), pH of 0.5% calcium carbonate (Ca Carb) (6.6±0.1) pH of 1% Ca Carb (7.6±0.1), pH of 0.5% sodium citrate (Na Cit) (6.2±0.3), and pH of 1% Na Cit (7.5±0.1). Incorporating 1% of Na Bicarb into RDST Formulation 2 (Table 1A) resulted in similar (p>0.05) pH values (7.9±0.1) of 1% Na Bicarb alone (8.1±0.3). Table 3.

Thus, Na Bicarb 1% increased the medium pH more than the rest of selected alkalinzing excipients in this experiment.

TABLE 3 pH measurement of different alkalizing excipients:

| | pH Reading | | |
|---|---|---|---|
| Concentration | Na Bicarbonate | Ca Carbonate | Na Citrate |
| 0.50% | 7.2 ± 0.2 | 6.6 ± 0.1 | 6.2 ± 0.3 |
| 1% | 8.1 ± 0.3§ | 7.6 ± 0.1 | 7.5 ± 0.1 |
| 1% with AS RDST | 7.9 ± 0.1 | — | — |

* Results are presented as mean ± SD
§ p < 0.05 from 0.5% Na Bicarbonate and all other excipients at 0.5% and 1%, but not different from 1% Na Bicarbonate incorporated into AS RDST.

The Effect of pH on the Sublingual Permeation of Atropine Sulfate (AS)

The cumulative atropine sulfate (AS) diffused per area ($\mu g/cm^2$) versus time, percentage of diffused AS, influx ($\mu g/cm^2/min$), and permeability (cm/min) for each RDST formulation were shown in FIGS. 2-5, respectively.

Mean (±SD) area under the curve (AUC) of cumulative AS diffused, J, and P at pH 8 (21069±586 $\mu g/cm^2$, 8.1±1.4 $\mu g/cm^2/min$, and 1±0.17 cm/min) were statistically higher ($p<0.05$) than at pH 5, 6.5, and 6.8 (8628±2738 µg/cm², 2.6±1 µg/cm/min, and 0.3±0.1 cm/min; 9144±539 µg/cm², 3.8±0.5 µg/cm²/min, and 0.5±0.07 cm/min; and 11685±1808 µg/cm², 4.4±1.3 µg/cm²/min, and 0.5±0.16 cm/min, respectively). Also, mean AUC of cumulative AS diffused, J, and P at pH 6.8 was statistically higher ($p<0.05$) than at pH 5. Table 4.

Thus, increasing the pH of the diffusion medium and the subsequent reduction in AS ionization degree resulted in a significant linear increase ($p<0.05$) in cumulative amount of AS diffused, AS influx (J), and permeability (P).

TABLE 4

Ex vivo diffusion of Atropine Sulfate (AS) Rapidly Disintegrating Tablets (RDSTs) at different pH medium:

|  | pH 5 | pH 6.5 | pH 6.8 | pH 8 |
| --- | --- | --- | --- | --- |
| $JAUC_{0-90}$ (µg/cm²/min) | 8628 ± 2738 | 9144 ± 539 | 11685 ± 1808 ¥ | 21069 ± 586 § |
| J (µg/cm²/min) | 2.6 ± 1 | 3.8 ± 0.5 | 4.4 ± 1.3 ¥ | 8.1 ± 1.4 § |
| P (cm/min) | 0.3 ± 0.1 | 0.5 ± 0.07 | 0.5 ± 0.16 ¥ | 1 ± 0.17 § |
| $t_L$ (min) | 1.4 ± 3 | 17.7 ± 8.9 | 4.8 ± 3 | 0.4 ± 1 |

* Results are presented as mean ± SD, J: influx, P: permeability
§ $p < 0.05$, from all
¥ $p < 0.05$, from pH 5

The Effect of Filler Grade, Alkalinizing Excipients, and Penetration Enhancers on the Sublingual Permeation of Atropine Sulfate The cumulative atropine sulfate (AS) diffused per area (µg/cm²) versus time, percentage of diffused AS, influx (µg/cm²/min), and permeability (cm/min) for each RDST formulation were shown in FIGS. 6-13, respectively.

Figure 10:
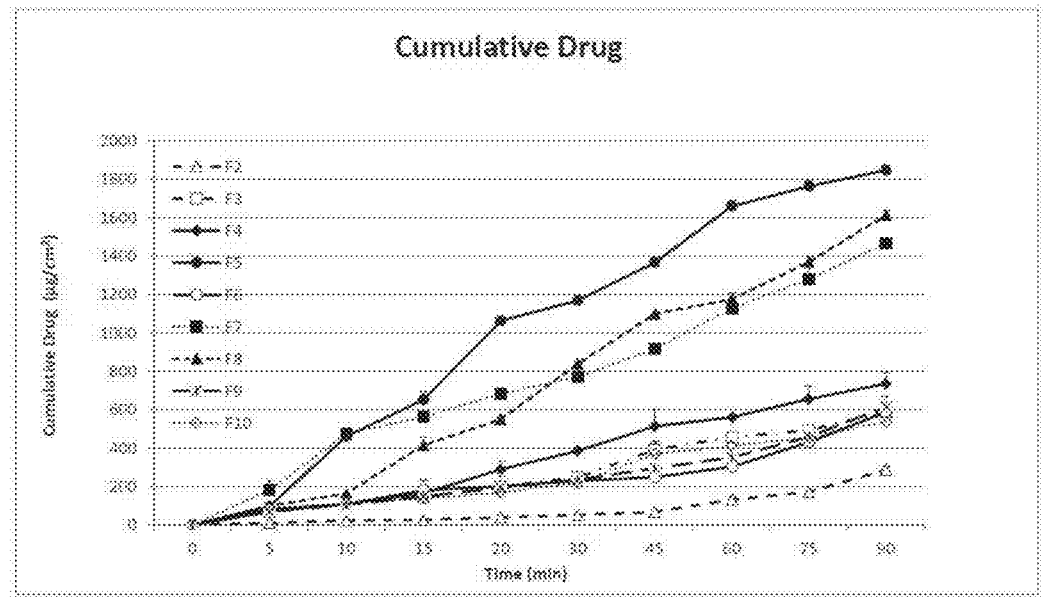
Figure 11:
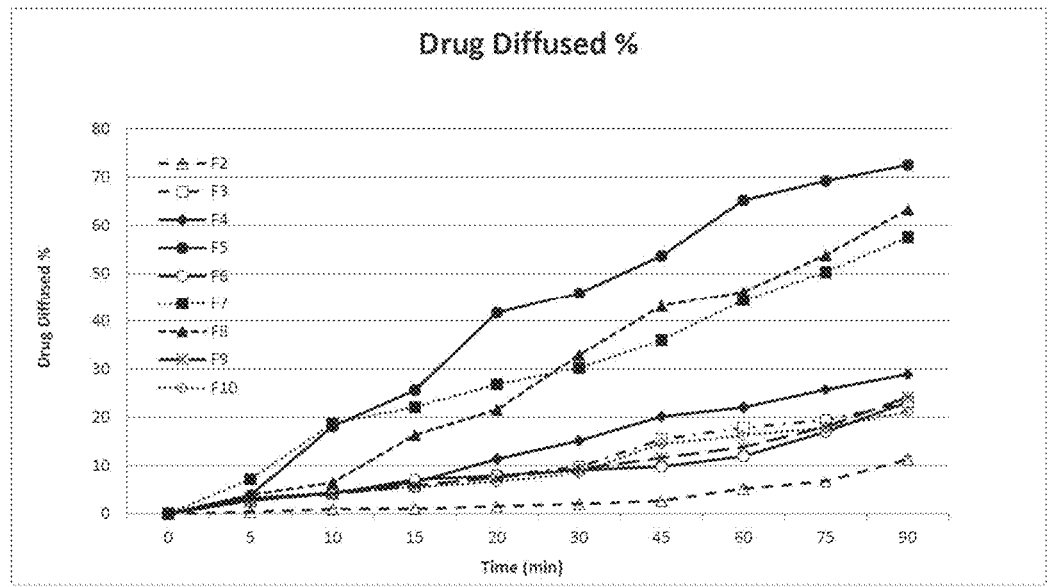
Figure 12:
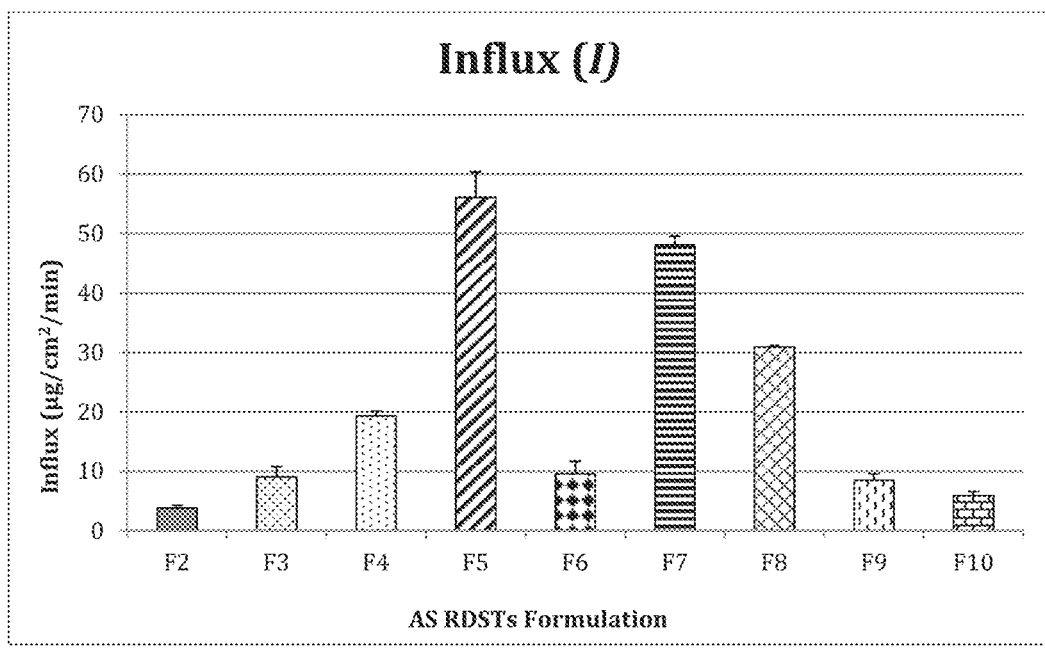
Figure 13:
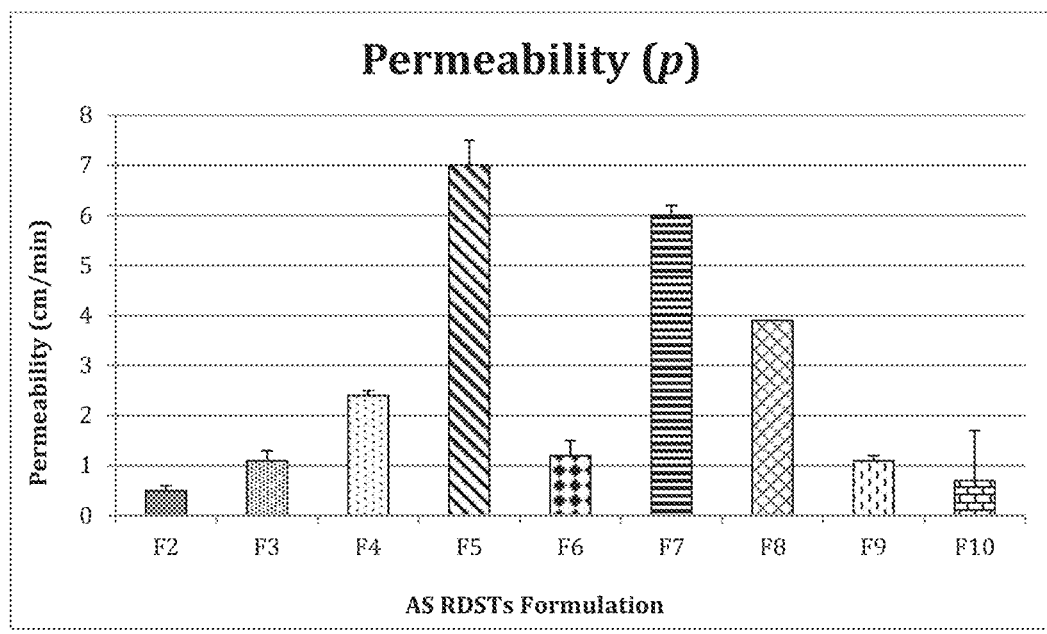

For ex viva diffusion, mean (±SD) area under the curve ($AUC_{0-90}$) of cumulative drug diffused from AS RDSTs with 0.5% SDS (F4), 1% SDS (F5), 16% PCC (F6), 15% Na Gly (F7), and 20% Na Gly (F8) were statistically higher ($p<0.05$) than F2, which has no alkalizer and no penetration enhancer (Tables 5A-5B and FIG. 10). The $AUC_{0-90}$ of AS RDSTs with transcellular enhancers (SDS and Na Gly) and an alkalizer (F4, F5, F7, and F8) were significantly higher ($p<0.05$) than formulations with paracellular enhancer (PCC) and an alkalizer (F6) and with enhancers alone (F9 and F10) (Tables 5A-5B and FIG. 10). Also, AS influx and permeability from AS RDSTs with transcellular enhancers and an alkalizer were significantly higher ($p<0.05$) than AS RDSTs with paracellular enhancer and an alkalizer, with enhancers alone, and the F2 formulation (Tables 5A-5B, Table 6, and FIGS. 12-13). Incorporating 1% SDS with 1% sodium bicarbonate achieved the highest enhancement in AS sublingual permeability ($p<0.05$) and increased AS permeability 17 folds compared to F2 formulation (Tables 5A-5B, Table 6, and FIG. 13). Incorporating alkalinizing excipient and a penetration enhancer to the RDST formulation had additive effect on enhancing the AS sublingual permeation.

Further, using MCC grade UF-702 as a filler instead of MCC PH-301 enhanced the RDST physical properties without affecting the sublingual permeation of AS.

TABLE 5A

Ex Vivo Diffusion of Atropine Sulfate (AS) Rapidly Disintegrating Tablets (RDSTs)*

|  | F1 | F2 | F3 | F4 | F5 |
| --- | --- | --- | --- | --- | --- |
| $JAUC_{0-90}$ (µg/cm²/min) | 11037 ± 3660 | 9144 ± 539 | 29689 ± 2296 ¥ | 40172 ± 1396 § | 104457 ± 2946 |
| J (µg/cm²/min) | 4.1 ± 1.4 | 3.8 ± 0.5 | 9.1 ± 1.7 ¥ | 19.3 ± 0.8 § | 56.1 ± 4.3 |
| P (cm/min) | 0.5 ± 0.2 | 0.5 ± 0.1 | 1.1 ± 0.2 ¥ | 2.4 ± 0.1 § | 7 ± 0.5 |
| $T_L$ (min) | 0.6 ± 0.9 | 17.7 ± 8.9 | 4.6 ± 1.3 | 7.7 ± 3.4 | 2.5 ± 0.5 |

TABLE 5B

Ex Vivo Diffusion of Atropine Sulfate (AS) Rapidly Disintegrating Tablets (RDSTs)*

|  | F6 | F7 | F8 | F9 | F10 |
| --- | --- | --- | --- | --- | --- |
| $JAUC_{0-90}$ (µg/cm²/min) | 25339 ± 1527 | 81742 ± 2131 | 84774 ± 908 | 27180 ± 2725.5 | 28228.29 ± 1488.139 |
| J (µg/cm²/min) | 9.6 ± 2.1 | 48.1 ± 1.5 | 30.9 ± 0.3 | 8.5 ± 1.1 | 5.9 ± 0.7 |
| P (cm/min) | 1.2 ± 0.3 | 6 ± 0.2 | 3.9 ± 0.0 | 1.1 ± 0.1 | 0.7 ± 1 |
| $T_L$ (min) | 7 ± 5 | 0 | 0 | 0 | 0 |

Tables 5A and 5B: Ex Vivo Diffusion of Atropine Sulfate (AS) Rapidly Disintegrating Sublingual Tablets (RDSTs)*
F1: 8 mg AS RDST using MCC PH-301; F2: 8 mg AS RDST using MCC UF-702; F3: 8 mg AS RDST with an alkalizer: F4-F8: 8 mg AS RDST with an alkalizer and a penetration enhancer (SDS 0.5%, SDS 1%, PCC 16%, Na Gly 15%, Na Gly 20%, respectively): and F9-F10: 8 mg AS RDST with a penetration enhancer (SDS 1% and Na Gly 20%, respectively).

*Results are presented as mean±SD, J: influx, P: permeability
§ p<0.05, from all
¥p<0.05, from F

TABLE 6

Influx and Permeability

| AS RDST Formulation | Influx | SD | Permeability | SD |
|---|---|---|---|---|
| F2 | 3.8 | 0.5 | 0.5 | 0.1 |
| F3 | 9.1 | 1.7 | 1.1 | 0.2 |
| F4 | 19.3 | 0.8 | 2.4 | 0.1 |
| F5 | 56.1 | 4.3 | 7.0 | 0.5 |
| F6 | 9.6 | 2.1 | 1.2 | 0.3 |
| F7 | 48.1 | 1.5 | 6.0 | 0.2 |
| F8 | 30.9 | 0.3 | 3.9 | 0.0 |
| F9 | 8.5 | 1.1 | 1.1 | 0.1 |
| F10 | 5.9 | 0.7 | 0.7 | 1.0 |

CONCLUSION

In conclusion, the improved formulation of atropine sulfate (AS) as rapidly-disintegrating sublingual tablets (RDSTs) was shown to be successful.

The selection of the grade of microcrystalline cellulose (MCC) filler can significantly impact RDSTs characteristics by enhancing both tablet breaking force and disintegration time in order to achieve better drug release and dissolution. These experiments showed that MCC grade UF-702 resulted in superior RDST characteristics without negatively affecting AS sublingual permeability.

The pH of the diffusion medium plays a major role in permeation of molecules across the sublingual membrane. Incorporating alkalinizing excipients in the RDST formulation has potential to increase the sublingual permeability and absorption of atropine sulfate (AS). Further, altering the pH of the diffusion medium to increase concentration of un-ionized AS can result in a significant increase in sublingual permeation (of AS). These experiments showed that modifying the pH of the sublingual membrane by adding an alkalinizing excipient into the AS RDSTs doubled the permeability of atropine sulfate.

Permeation/Penetration enhancers can be used be to enhance permeation of molecules across the sublingual membrane by passive diffusion. These experiments showed that adding a penetration enhancer into the RDST formulation, in addition to the alkalinizing agent, enhanced permeability of atropine sulfate (AS) by more than 17 folds.

The herein described atropine sulfate (AS) rapidly-disintegrating sublingual tablets (RDSTs) of improved formulation provide a non-invasive sublingual delivery of atropine sulfate for the treatment of acute organophosphate (OP) toxicity as a potential alternative (to the conventional parenteral delivery), patient-friendly, convenient, and cost-effective dosage form.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not intended to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The compositions, rapidly-disintegrating sublingual tablets (RDSTs), atropine sulfate rapidly-disintegrating sublingual tablets (AS RDSTs), atropine sulfate rapidly-disintegrating sublingual tablets (AS RDSTs) of improved formulation, therapeutic compositions and methods, pharmaceutical tablets, methods, procedures, and techniques described herein are presently representative of the preferred embodiments, are intended to be exemplary and are not intended as limitations on the scope. Changes therein and other uses will occur to those skilled in the art which are encompassed within the spirit of the invention. Although the invention has been described in connection with specific, preferred embodiments, it should be understood that the invention as ultimately claimed should not be unduly limited to such specific embodiments. Indeed various modifications of the described modes for carrying out the invention which are obvious to those skilled in the art are intended to be within the scope of the invention.

What is claimed is:

1. A pharmaceutical composition comprising atropine sulfate and at least one pharmaceutically acceptable excipient, the pharmaceutical composition formulated for rapid disintegration following buccal or sublingual administration,
   wherein the pharmaceutical composition is configured to fully disintegrate in less than one minute in the mouth and configured to create an environment of about pH 8 at the site of absorption within the mouth; and
   wherein the pharmaceutical composition comprises from about 1 to about 20 wt % of atropine sulfate, from about 20 to about 95 wt % of microcrystalline cellulose, from about 1 to about 15 wt % hydroxypropyl cellulose, from about 0.5 to about 3 wt % magnesium stearate, from about 0.5 to about 5 wt % of sodium bicarbonate, and from about 0.5 to about 3 wt % of sodium dodecyl sulfate (SDS).

2. The pharmaceutical composition in accordance with claim 1, wherein the hydroxypropyl cellulose is low substituted.

3. The pharmaceutical composition in accordance with claim 1, wherein the pharmaceutical composition comprises about 1 wt % of sodium bicarbonate.

4. A pharmaceutical composition comprising atropine sulfate and at least one pharmaceutically acceptable excipient, the pharmaceutical composition formulated for rapid disintegration following buccal or sublingual administration,
   wherein the pharmaceutical composition is configured to fully disintegrate in less than one minute in the mouth and configured to create an environment of about pH 8 at the site of absorption within the mouth, and
   wherein the pharmaceutical composition comprises about 16 wt % of atropine sulfate, about 72 wt % of microcrystalline cellulose, about 8 wt % hydroxypropyl cellulose, about 1 wt % of magnesium stearate, about 2 wt % of sodium bicarbonate, and about 1 wt % of sodium dodecyl sulfate.

5. Atropine sulfate tablets formulated for rapid disintegration following buccal or sublingual administration comprising the pharmaceutical composition of claim 1.

* * * * *